US012640233B2

(12) United States Patent
Rizk

(10) Patent No.: US 12,640,233 B2
(45) Date of Patent: *May 26, 2026

(54) METHOD FOR THE COMPRESSION OF GENOME SEQUENCE DATA

(71) Applicant: Illumina, Inc., San Diego, CA (US)

(72) Inventor: Guillaume Alexandre Pascal Rizk, Rennes (FR)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/540,814

(22) Filed: Dec. 14, 2023

(65) Prior Publication Data

US 2024/0194296 A1 Jun. 13, 2024

Related U.S. Application Data

(63) Continuation of application No. 16/567,211, filed on Sep. 11, 2019, now abandoned.

(51) Int. Cl.
*G16B 30/10* (2019.01)
*G06F 16/23* (2019.01)
(Continued)

(52) U.S. Cl.
CPC ......... *G16B 30/10* (2019.02); *G06F 16/2365* (2019.01); *G16B 20/20* (2019.02);
(Continued)

(58) Field of Classification Search
CPC ........ G16B 30/10; G16B 20/20; G16B 30/20; G16B 50/50
See application file for complete search history.

(56) References Cited

U.S. PATENT DOCUMENTS 5,859,972 A 1/1999 Subramaniam et al.
5,964,072 A 10/1999 Rasmussen
(Continued)

FOREIGN PATENT DOCUMENTS

AU 2014335877 A1 5/2016
CN 102308206 A 1/2012
(Continued)

OTHER PUBLICATIONS

Wandelt, Sebastian, and Ulf Leser. "Adaptive efficient compression of genomes." Algorithms for Molecular Biology 7 (2012): 1-9. (Year: 2012).*

(Continued)

*Primary Examiner* — Jesse P Frumkin
(74) *Attorney, Agent, or Firm* — Matthew M. Hulihan, Esq.; Heslin Rothenberg Farley & Mesiti P.C.

(57) ABSTRACT

Systems, methods, computer programs, and hardware circuits for compressing genomic sequence data. In one aspect, the method can include obtaining a read record, determining whether the read record corresponds to a read that is perfectly mapped to a reference sequence or imperfectly mapped to the reference sequence, based on determining that the read record corresponds to a read that is imperfectly mapped to the reference sequence whether a number of mismatches of the imperfectly mapped read does not exceed a predetermined threshold number of mismatches, and based on determining that the number of mismatches does not exceed the predetermined threshold number of mismatches, (i) obtaining an offset from a previous mismatch that is lower than a maximum encodable offset value and (ii) encoding each mismatch of the imperfectly mapped read and the offset from the previous mismatch of the read into a record having a size of 1 byte.

28 Claims, 2 Drawing Sheets

CASE 2 : GLOBAL ALIGNMENT, MISMATCH LIST REQUIRING "FAKE MISMATCH"

REFERENCE SEQUENCE — A — T — C
READ — T — T — G
MISMATCH 63 49 MISMATCH
"FAKE" MISMATCH

MISMATCH LIST IS: POSITION 22: T, POSITION 134: G
ENCODED AS: <22,T>, <63,G> <49,G> RESULTING IN ENCODING 91,255,198

(51) Int. Cl.

| | |
|---|---|
| *G16B 20/20* | (2019.01) |
| *G16B 30/20* | (2019.01) |
| *G16B 45/00* | (2019.01) |
| *G16B 50/50* | (2019.01) |

(52) U.S. Cl.
CPC ............. *G16B 30/20* (2019.02); *G16B 45/00* (2019.02); *G16B 50/50* (2019.02)

(56) References Cited

U.S. PATENT DOCUMENTS

| | | | |
|---|---|---|---|
| 5,964,860 | A | 10/1999 | Peterson et al. |
| 6,112,288 | A | 8/2000 | Ullner |
| 6,253,529 | B1 | 7/2001 | De Boer |
| 6,681,186 | B1 | 1/2004 | Denisov et al. |
| 7,135,701 | B2 | 11/2006 | Amin et al. |
| 7,533,068 | B2 | 5/2009 | Maassen van den Brink et al. |
| 7,680,790 | B2 | 3/2010 | Indeck et al. |
| 7,917,299 | B2 | 3/2011 | Buhler et al. |
| 7,917,302 | B2 | 3/2011 | Rognes |
| 7,945,668 | B1 | 5/2011 | Nucci et al. |
| 7,948,015 | B2 | 5/2011 | Rothberg et al. |
| 7,969,805 | B2 | 6/2011 | Thom et al. |
| 8,190,548 | B2 | 5/2012 | Choi |
| 8,195,596 | B2 | 6/2012 | Rose et al. |
| 8,209,130 | B1 | 6/2012 | Kennedy et al. |
| 8,217,433 | B1 | 7/2012 | Fife |
| 8,280,640 | B2 | 10/2012 | Levin et al. |
| 8,340,914 | B2 * | 12/2012 | Gatewood ............. G06F 16/215 707/700 |
| 8,445,945 | B2 | 5/2013 | Rothberg et al. |
| 8,524,487 | B2 | 9/2013 | Fife |
| 8,558,288 | B2 | 10/2013 | Rothberg et al. |
| 8,560,282 | B2 | 10/2013 | Macready et al. |
| 8,594,951 | B2 | 11/2013 | Homer |
| 8,620,923 | B1 | 12/2013 | Wormley et al. |
| 8,700,689 | B2 | 4/2014 | Macready et al. |
| 8,738,105 | B2 | 5/2014 | Berkley et al. |
| 8,751,166 | B2 | 6/2014 | Friedlander et al. |
| 8,798,936 | B2 | 8/2014 | Bauer et al. |
| 8,812,243 | B2 * | 8/2014 | Cardonha ............. G16B 30/00 707/700 |
| 8,847,799 | B1 | 9/2014 | Kennedy et al. |
| 8,936,763 | B2 | 1/2015 | Rothberg et al. |
| 9,014,989 | B2 | 4/2015 | McMillen et al. |
| 9,026,574 | B2 | 5/2015 | Macready et al. |
| 9,235,680 | B2 | 1/2016 | Rooyen et al. |
| 9,322,872 | B2 | 4/2016 | Hill |
| 9,355,365 | B2 | 5/2016 | Berkley et al. |
| 9,405,876 | B2 | 8/2016 | Macready et al. |
| 9,483,610 | B2 | 11/2016 | McMillen et al. |
| 9,576,103 | B2 | 2/2017 | McMillen et al. |
| 9,618,474 | B2 | 4/2017 | van Rooyen et al. |
| 9,679,104 | B2 | 6/2017 | van Rooyen et al. |
| 9,792,405 | B2 | 10/2017 | van Rooyen et al. |
| 10,049,179 | B2 | 8/2018 | van Rooyen et al. |
| 10,068,052 | B2 | 9/2018 | van Rooyen et al. |
| 10,068,183 | B1 | 9/2018 | van Rooyen |
| 10,090,857 | B2 | 10/2018 | Bhola et al. |
| 10,122,379 | B1 * | 11/2018 | Ciarlini ................... H03M 7/30 |
| 10,179,937 | B2 | 1/2019 | Babiarz et al. |
| 11,049,588 | B2 | 6/2021 | van Rooyen et al. |
| 11,527,307 | B2 | 12/2022 | Rizk et al. |
| 11,776,663 | B2 | 10/2023 | Rizk et al. |
| 12,080,385 | B2 | 9/2024 | Rizk et al. |
| 2003/0033279 | A1 | 2/2003 | Gibson et al. |
| 2003/0033501 | A1 | 2/2003 | Cooke et al. |
| 2003/0039362 | A1 | 2/2003 | Califano et al. |
| 2003/0104470 | A1 | 6/2003 | Fors et al. |
| 2004/0024536 | A1 | 2/2004 | Rognes |
| 2004/0059721 | A1 | 3/2004 | Patzer |
| 2004/0098203 | A1 | 5/2004 | Rognes |
| 2004/0126840 | A1 | 7/2004 | Cheng et al. |
| 2004/0142463 | A1 | 7/2004 | Walker et al. |
| 2004/0153255 | A1 * | 8/2004 | Ahn ....................... G16B 30/10 702/20 |
| 2005/0060195 | A1 | 3/2005 | Bessette et al. |
| 2005/0131649 | A1 | 6/2005 | Larsen et al. |
| 2005/0228595 | A1 | 10/2005 | Cooke et al. |
| 2005/0267693 | A1 * | 12/2005 | Allard ................... G16B 30/10 702/20 |
| 2006/0225165 | A1 | 10/2006 | Maassen van den Brink et al. |
| 2007/0038381 | A1 | 2/2007 | Melchior et al. |
| 2007/0078897 | A1 | 4/2007 | Hayashi et al. |
| 2007/0088510 | A1 | 4/2007 | Li et al. |
| 2007/0196816 | A1 | 8/2007 | Schwartz et al. |
| 2008/0005024 | A1 | 1/2008 | Kirkwood |
| 2008/0050782 | A1 | 2/2008 | Selifonov et al. |
| 2008/0086274 | A1 | 4/2008 | Chamberlain et al. |
| 2008/0176750 | A1 | 7/2008 | Rose et al. |
| 2008/0250016 | A1 | 10/2008 | Farrar |
| 2009/0121215 | A1 | 5/2009 | Choi |
| 2009/0125248 | A1 | 5/2009 | Shams et al. |
| 2009/0171647 | A1 | 7/2009 | Mannava et al. |
| 2009/0253130 | A1 | 10/2009 | Yoo |
| 2009/0270277 | A1 | 10/2009 | Glick et al. |
| 2010/0077267 | A1 | 3/2010 | Perego et al. |
| 2010/0082805 | A1 | 4/2010 | Orton et al. |
| 2010/0085827 | A1 | 4/2010 | Thom et al. |
| 2010/0169313 | A1 | 7/2010 | Kenedy et al. |
| 2010/0281401 | A1 | 11/2010 | Tebbs et al. |
| 2010/0327847 | A1 | 12/2010 | Leiber et al. |
| 2011/0004413 | A1 | 1/2011 | Carnevali et al. |
| 2011/0093581 | A1 | 4/2011 | Ventatachalm |
| 2011/0184235 | A1 | 7/2011 | Schostek et al. |
| 2011/0227043 | A1 | 9/2011 | Guo et al. |
| 2011/0231446 | A1 | 9/2011 | Buhler et al. |
| 2011/0288785 | A1 | 11/2011 | Tembe |
| 2012/0001615 | A1 | 1/2012 | Levine |
| 2012/0089339 | A1 | 4/2012 | Ganeshalingam et al. |
| 2012/0102041 | A1 | 4/2012 | Park et al. |
| 2012/0109849 | A1 | 5/2012 | Chamberlain et al. |
| 2012/0135394 | A1 | 5/2012 | Kim et al. |
| 2012/0149981 | A1 | 6/2012 | Khait et al. |
| 2012/0214172 | A1 | 8/2012 | Chen et al. |
| 2013/0018599 | A1 | 1/2013 | Peng |
| 2013/0031092 | A1 | 1/2013 | Bhola et al. |
| 2013/0091121 | A1 | 4/2013 | Galinsky |
| 2013/0110407 | A1 | 5/2013 | Baccash et al. |
| 2013/0124100 | A1 | 5/2013 | Drmanac et al. |
| 2013/0144925 | A1 | 6/2013 | Macready et al. |
| 2013/0157870 | A1 | 6/2013 | Pushkarev et al. |
| 2013/0194882 | A1 | 8/2013 | Ishii et al. |
| 2013/0204851 | A1 | 8/2013 | Bhola et al. |
| 2013/0245958 | A1 | 9/2013 | Forster et al. |
| 2013/0254202 | A1 | 9/2013 | Friedlander et al. |
| 2013/0275486 | A1 | 10/2013 | Dickinson et al. |
| 2013/0296175 | A1 | 11/2013 | Rafnar et al. |
| 2013/0297221 | A1 | 11/2013 | Johnson et al. |
| 2013/0307029 | A1 | 11/2013 | Xu et al. |
| 2013/0311106 | A1 | 11/2013 | White et al. |
| 2013/0316331 | A1 | 11/2013 | Isakov et al. |
| 2013/0324417 | A1 | 12/2013 | Kennedy et al. |
| 2013/0332081 | A1 | 12/2013 | Reese et al. |
| 2013/0338012 | A1 | 12/2013 | Sulem et al. |
| 2013/0338934 | A1 | 12/2013 | Asadi et al. |
| 2014/0024537 | A1 | 1/2014 | Rigatti et al. |
| 2014/0025312 | A1 | 1/2014 | Chin et al. |
| 2014/0033125 | A1 | 1/2014 | Merel |
| 2014/0045705 | A1 | 2/2014 | Bustamante et al. |
| 2014/0046926 | A1 | 2/2014 | Walton |
| 2014/0051588 | A9 | 2/2014 | Drmanac et al. |
| 2014/0081665 | A1 | 3/2014 | Holmes |
| 2014/0114582 | A1 | 4/2014 | Mittelman et al. |
| 2014/0121116 | A1 | 5/2014 | Richards et al. |
| 2014/0164516 | A1 | 6/2014 | Maltbie et al. |
| 2014/0200166 | A1 | 7/2014 | Van Rooyen et al. |
| 2014/0236490 | A1 | 8/2014 | Van Rooyen et al. |
| 2014/0297196 | A1 | 10/2014 | Olson |
| 2014/0304276 | A1 | 10/2014 | Boyce |
| 2014/0309944 | A1 | 10/2014 | van Rooyen et al. |
| 2014/0310215 | A1 | 10/2014 | Trakadis |
| 2014/0316716 | A1 | 10/2014 | Jiang et al. |

(56) References Cited

U.S. PATENT DOCUMENTS

| | | | |
|---|---|---|---|
| 2014/0337052 A1 | 11/2014 | Pellini et al. | |
| 2014/0350968 A1 | 11/2014 | Hahn et al. | |
| 2014/0361911 A1 | 12/2014 | Kennedy et al. | |
| 2014/0368550 A1 | 12/2014 | Vaske et al. | |
| 2014/0371109 A1 | 12/2014 | McMillen et al. | |
| 2014/0371110 A1 | 12/2014 | Van Rooyen et al. | |
| 2015/0066824 A1 | 3/2015 | Harris et al. | |
| 2015/0123600 A1 | 5/2015 | Groat et al. | |
| 2015/0142334 A1 | 5/2015 | Mishra | |
| 2015/0149510 A1 | 5/2015 | Kennedy et al. | |
| 2015/0154406 A1 | 6/2015 | Naehrig et al. | |
| 2015/0211055 A1 | 7/2015 | Apte et al. | |
| 2015/0227686 A1 | 8/2015 | Sheinin et al. | |
| 2015/0227697 A1 | 8/2015 | Nelson et al. | |
| 2015/0248525 A1 | 9/2015 | Ury et al. | |
| 2015/0286495 A1 | 10/2015 | Lee | |
| 2015/0310163 A1 | 10/2015 | Kingsmore et al. | |
| 2015/0339437 A1 | 11/2015 | McMillen et al. | |
| 2015/0363550 A1 | 12/2015 | Green, Jr. et al. | |
| 2016/0046986 A1 | 2/2016 | Eltoukhy et al. | |
| 2016/0057246 A1 | 2/2016 | Krishnaiahsetty | |
| 2016/0092631 A1 | 3/2016 | Yandell et al. | |
| 2016/0140290 A1 | 5/2016 | Rooyen et al. | |
| 2016/0154795 A1 | 6/2016 | Kennedy et al. | |
| 2016/0171153 A1 | 6/2016 | Van Rooyen et al. | |
| 2016/0178569 A1 | 6/2016 | Hoffman et al. | |
| 2016/0188793 A1 | 6/2016 | Muzzey et al. | |
| 2016/0283407 A1 | 9/2016 | Van Rooyen et al. | |
| 2016/0306923 A1 | 10/2016 | van Rooyen et al. | |
| 2017/0068776 A1 | 3/2017 | Godinez-Moreno et al. | |
| 2017/0107576 A1 | 4/2017 | Babiarz et al. | |
| 2017/0116216 A1 | 4/2017 | Kennedy et al. | |
| 2017/0124254 A1 | 5/2017 | Rooyen et al. | |
| 2017/0237445 A1 | 8/2017 | Cox et al. | |
| 2017/0270245 A1 | 9/2017 | van Rooyen et al. | |
| 2017/0308644 A1 | 10/2017 | van Rooyen et al. | |
| 2017/0317689 A1* | 11/2017 | Nam | H03M 7/6011 |
| 2017/0357665 A1 | 12/2017 | Olivares-Amaya et al. | |
| 2018/0121601 A1 | 5/2018 | Hahm et al. | |
| 2018/0152535 A1 | 5/2018 | Sade et al. | |
| 2018/0189444 A1 | 7/2018 | van Rooyen et al. | |
| 2018/0196916 A1 | 7/2018 | van Rooyen et al. | |
| 2018/0196917 A1 | 7/2018 | van Rooyen et al. | |
| 2018/0239865 A1 | 8/2018 | van Rooyen et al. | |
| 2018/0240032 A1 | 8/2018 | van Rooyen | |
| 2019/0130998 A1 | 5/2019 | van Rooyen et al. | |
| 2019/0171963 A1 | 6/2019 | van Rooyen | |
| 2019/0172558 A1 | 6/2019 | van Rooyen et al. | |
| 2019/0214111 A1 | 7/2019 | Alberti et al. | |
| 2019/0385702 A1 | 12/2019 | Alberti et al. | |
| 2020/0051664 A1* | 2/2020 | Zoia | H04N 19/91 |
| 2021/0074381 A1* | 3/2021 | Rizk | G06F 16/2365 |
| 2021/0193261 A1 | 6/2021 | Van Rooyen et al. | |
| 2021/0257052 A1 | 8/2021 | Van Rooyen et al. | |
| 2021/0313014 A1 | 10/2021 | van Rooyen | |
| 2022/0139502 A1 | 5/2022 | Rizk et al. | |
| 2022/0415441 A1* | 12/2022 | Rizk | G16B 20/20 |
| 2023/0040143 A1 | 2/2023 | Rizk et al. | |
| 2023/0290443 A1 | 9/2023 | Rizk | |
| 2024/0062853 A1 | 2/2024 | Rizk et al. | |
| 2024/0395359 A1 | 11/2024 | Onuchic et al. | |
| 2024/0395363 A1 | 11/2024 | Han et al. | |
| 2024/0420804 A1 | 12/2024 | Rizk et al. | |
| 2025/0046399 A1 | 2/2025 | Rizk et al. | |

FOREIGN PATENT DOCUMENTS

| | | |
|---|---|---|
| CN | 102521528 A | 6/2012 |
| CN | 103293209 A | 9/2013 |
| CN | 103336916 A | 10/2013 |
| CN | 104428425 A | 3/2015 |
| CN | 107851137 A | 3/2018 |
| CN | 105051741 B | 4/2018 |
| CN | 110168649 A | 8/2019 |
| EP | 2313523 A2 | 4/2011 |
| EP | 2759952 A1 | 7/2014 |
| EP | 3317440 A4 | 3/2019 |
| EP | 3465507 B1 | 9/2021 |
| JP | 2007-108949 A | 4/2007 |
| JP | 2016-514291 A | 5/2016 |
| JP | 2014-146318 A | 8/2021 |
| KR | 1020130088512 A | 8/2013 |
| RU | 2282242 C2 | 8/2006 |
| RU | 2015144109 A | 4/2017 |
| WO | WO 2006/110855 A2 | 10/2006 |
| WO | WO 2011/149534 A2 | 12/2011 |
| WO | WO 2012/122546 A2 | 9/2012 |
| WO | WO 2013/128371 A2 | 9/2013 |
| WO | WO 2014/060305 A1 | 4/2014 |
| WO | WO 2014/074246 A1 | 5/2014 |
| WO | WO 2014/113736 A1 | 7/2014 |
| WO | WO 2014/121091 A1 | 8/2014 |
| WO | WO 2014/186604 A1 | 11/2014 |
| WO | WO 2015/051006 A2 | 4/2015 |
| WO | WO 2015/089333 A1 | 6/2015 |
| WO | WO 2015/100427 A1 | 7/2015 |
| WO | WO 2015/123600 A1 | 8/2015 |
| WO | WO 2015/166389 A1 | 11/2015 |
| WO | WO 2016/051429 A1 | 4/2016 |
| WO | WO 2016/061396 A1 | 4/2016 |
| WO | WO 2016/168371 A1 | 10/2016 |
| WO | WO 2017/004589 A1 | 1/2017 |
| WO | WO 2018/068829 | 4/2018 |
| WO | WO 2018/071054 A1 | 4/2018 |
| WO | WO 2018/071078 A1 | 4/2018 |
| WO | WO 2020/023882 A1 | 1/2020 |
| WO | WO 2002/086161 A1 | 10/2022 |

OTHER PUBLICATIONS

CA Office Action in Canadian Appln. No. 3,148,960, mailed on Dec. 14, 2023, 7 pages.

CA Office Action in Canadian Appln. No. 3,148,976, mailed on Jan. 5, 2024, 6 pages.

EP Extended European Search Report in European Appln. No. 23195421.5, mailed on Mar. 7, 2024, 12 pages.

Grabowski et al., "Engineering Relative Compression of Genomes", Arxiv.org, Cornell University Library, Mar. 11, 2011, 1-12.

Hach et al., "DeeZ: reference-based compression by local assembly," Nature Methods, Nov. 2014, 11(11):1082-4.

Law et al., "Application of signal processing for DNA sequence compression", IET Signal Processing, Aug. 13, 2019, 1-12.

PCT International Preliminary Report on Patentability in International Appln. No. PCT/US2020/050584, dated Nov. 25, 2021, 9 pages.

PCT International Preliminary Report on Patentability in International Appln. No. PCT/US2020/050586, dated Nov. 25, 2021, 13 pages.

PCT International Search Report and Written Opinion in International Appln. No. PCT/US2020/050584, dated Nov. 20, 2020, 68 pages.

PCT International Search Report and Written Opinion in International Appln. No. PCT/US2020/050586, dated Nov. 26, 2020, 68 pages.

RU Office Action in Russian Appln. No. 2022101850, dated Nov. 25, 2022, 11 pages (with English translation).

RU Office Action in Russian Appln. No. 2022101852, dated Jan. 31, 2023, 13 pages (with English translation).

Wandelt et al., "Adaptive efficient compression of genomes", Algorithms Mol Biol. Nov. 12, 2012, 7(1):9 pages.

Wandelt et al., "FRESCO: Referential compression of highly similar sequences," IEEE/ACM Transactions on Computational Biology and Bioinformatics, Oct. 1, 2013, 10(5):1275-88.

CA Office Action in Canadian Appln. No. 3148976, mailed on Oct. 15, 2024, 6 pages.

EP Office Action in European Appln. No. 20780856.9, mailed on Aug. 20, 2024, 10 pages.

JP Office Action in Japanese Appln. No. 2022-515563, mailed on Oct. 7, 2024, 9 pages (with English translation).

(56) References Cited

OTHER PUBLICATIONS

JP Office Action in Japanese Appln. No. 2022-515895, mailed on Sep. 30, 2024, pages (with English translation).

Zyuzin et al., "Approach to Compression DNA Sequences Using an Algorithm Binary Achiever," Materials of Scientific and Practical Internet Conferences, Nov. 25-26, 2014, 5 pages.

CN Office Action in Chinese Appln. No. 202080062727.6, mailed on Dec. 17, 2024, 16 pages (with English translation).

US Office Action in U.S. Appl. No. 16/567,201, mailed on Sep. 14, 2023, 17 pages.

[No Author], "Chap 5 Dictionary Techniques," Aug. 23, 2016, retrieved from URL <http://se.csie.dyu.edu.tw/lairrol/files/DC/chap5.pdf>, 55 pages.

[No Author], "History of Lossless Data Compression Algorithms," Jul. 28, 2014, retrieved from URL <http://ieeeghn.org/wiki/index.php?title=History_of_Lossless Data_Co+A7mpression_Algorithms &oldid=96464&printable=yes&useskin=vector>, 16 pages.

Abbas et al., "Combining Executin Pipelines to Improve Parallel Implementation of HMMER on FPGA," Microprocessors and Microsystems, Jun. 2015, 39(7):457-470.

Ahmed et al., "A Comparison of Seed-and-Extend Techniques in Modern DNA Read Alignment Algorithms," Paper, Presented at the Proceedings on BIBM: Bioinformatics and Biomedicine, Shenzhen, China, Dec. 15-18, 2016, pp. 1421-1428.

akita.com, "Science of Akita, RNA Sequence Manuals" Dec. 18, 2014, retrieved Sep. 4, 2024 from URL <https://www.dbp.akita-pu.ac.jp/esuzuki/RNASeq_manuals/30ddbjing_Pipeline.pdf>, 2-55 (no translation available).

Al Junid et al., "Development of Novel Data Compression Technique for Accelerate DNA Sequence Alignment Based on Smith-Waterman Algorithm," Paper, Presented at the Third UKSim European Symposium on Computer Modeling and Simulation, Athens, Greece, Nov. 25-27, 2009; IEEE, Dec. 2009, pp. 181-186.

Al Junid et al., "Optimization of DNA Sequences Data for Accelerate DNA Sequences Alignment on FPGA," Paper, Presented at the 2010 Fourth Asia International Conference on Mathematical/Analytical Modelling and Computer Simulation, Kota Kinabalu, Malaysia, May 26-28, 2010; IEEE, Jun. 2010, pp. 231-236.

Al Tera Corp, "Implementation of the Smith-Waterman Algorithm on a Reconfigurable Supercomputing Platform," White Paper, Sep. 2007, version 1, 18 pages.

Alachiotis et al., "Accelerating Phylogeny-Aware Short DNA Read Alignment with FPGAs," The Exelixis Lab, Heidelberg Institute for Theoretical Studies, Heidelberg, Germany, 2011, 8 pages.

Alser et al., "Technology dictates algorithms: recent developments in read alignment," Genome Biology, Aug. 2021, 22(1):249, 74 pages.

Angiuoli et al., "Mugsy: fast multiple alignment of closely related whole genomes," Bioinformatics, published online Dec. 9, 2010, published in print 2011, retrieved on May 25, 2016, retrieved from URL <http://bioinformatics.oxfordjournals.org/content/27/31334.full>, 27(3):334-342.

Anonymous: "FPGA-accelerated Bioinformics at #ASHG-Dragen Aligner from Edico Genome," Oct. 20, 2014, XP055360856, retrieved on Mar. 31, 2017, retrieved from URL <http://moolog.us/blogs/glob/2014/210/20/fpga-accelerated-bioinform ics-at-ashg-dragenaliqner- from-edico-genome/#>, 7 pages.

AU Office Action in Australian Appln. No. 2017207317, dated Aug. 31, 2022, 6 pages.

AU Office Action in Australian Appln. No. 2017207317, mailed on Sep. 3, 2021, 6 pages.

AU Office Action in Australian Appln. No. 2022228089, mailed on Oct. 3, 2023, 5 pages.

AU Office Action in Australian Appln. No. 2022228089, mailed on Sep. 23, 2024, 3 pages.

AU Office Action in Australian Appln. No. 2022252718, mailed on Jul. 19, 2024, 3 pages.

AU Office Action in Australian Appln. No. 2022252718, mailed on Jul. 27, 2023, 3 pages.

Benkrid et al., "A highly parameterized and efficient FPGA-based skeleton for pairwise biological sequence alignment," IEEE Transactions on VLSI Systems, IEEE Educational Activities Dept. Piscataway, NJ, Apr. 2009, pp. 561-570 (1-12).

Benkrid et al., "High Performance Biological Pairwise Sequence Alignment: FPGA versus GPU versus Cell BE versus GPP," International Journal of Reconfigurable Computing, 2012, 2012:752910, 16 pages.

Benkrid et. al., "A High Performance Reconfigurable Core for Motif Searching Using Profile HMM," Paper, Presented at the 2008 NASA/ESA Conference on Adaptive Hardware and Systems, Noordwijk, Netherlands, Jun. 22-25, 2008; IEEE, Aug. 2008, pp. 285-292.

Benoit et al., "NGS Data Compression," Algorithms for Next-Generation Sequencing Data, Dec. 2017, pp. 91-115.

Booth et al., "Bio-Linux as a tool for bioinformatics training," Paper, Presented at the 2012 IEEE 12th International Conference on Bioinformatics & Bioengineering (BIBE), Larnaca, Cyprus, Nov. 11-13, 2012; IEEE, Jan. 2013, pp. 578-582.

BR Office Action in Brazilian Appln. No. 1220230005996, mailed on Sep. 16, 2024, 11 pages (with English translation).

BR Office Action in Brazilian appln. no. BR112018014086-4, mailed on Sep. 16, 2022, 8 pages (with English translation).

Buyukkurt et al., "Compiler Generated Systolic Arrays for Wavefront Algorithm Acceleration on FPGAs," Paper, Presented at the 2008 International Conference on Field Programmable Logic and Applications, Heidelberg, Germany, Sep. 8-10, 2008; IEEE, Sep. 2008, 4 pages.

CA Office Action in Canadian Appln. No. 3,008,176, mailed on Feb. 21, 2023, 5 pages.

CA Office Action in Canadian Appln. No. 3,026,644, mailed on Jul. 21, 2023, 4 pages.

CA Office Action in Canadian Appln. No. 3,174,208, mailed on Apr. 11, 2024, 5 pages.

CA Office Action in Canadian Appln. No. 3026644, mailed on Apr. 10, 2024, 7 pages.

Cánovas et al., "Lossy compression of quality scores in genomic data," Bioinformatics, Aug. 2014, 30(15):2130-2136.

Carneiro, "Accelerating Variant Calling," Powerpoint Presentation, Broad Institute, Intel Genomic Sequencing Pipeline Workshop, Mount Sinai, New York, Dec. 10, 2013, 26 pages.

Chang et al., "Exploring Sequence Alignment Algorithms on FPGA-based Heterogeneous B Architectures," Paper, Presented at the International Work-Conference on Bioinformatics and Biomedical Engineering, Granada, Spain, Apr. 7-9, 2014, pp. 330-341.

Chang et al., "FPGA-based Heterogeneous Architecture for Sequence Alignment," The XIV Microelectronics, Students Forum, Sep. 2014, 4 pages.

Chang et al., "The SMEM Seeding Acceleration for DNA Sequence Alignment," Paper, Presented at the 2016 IEEE 24th Annual International Symposium on Field-Programmable Custom Computing Machines (FCCM), Washington D.C., USA, May 1-3, 2016; IEEE, Aug. 2016, pp. 32-39.

Choi et al., "A quantitative analysis on microarchitectures of modern CPU-FPGA platforms," Paper, Presented at the DAC '16: Proceedings of the 53rd Annual Design Automation Conference, Austin, Texas, Jun. 5-9, 2016, 6 pages.

Choi et al., "Impact of Cache Architectures and Interface on Performance and Area of FPGA-Based Processor/Parallel-Accelerator Systems," Paper, Presented at the 2012 IEEE 20th International Symposium on Field-Programmable Custom Computing Machines (FCCM), Toronto, Canada, Apr. 29-May 1, 2012; IEEE, Jul. 2012, pp. 17-24.

Chrysanthou et al., "Parallel Accelerators for GlimmerHMM Bioinformatics Algorithm," Paper, Presented at the 2011 Design, Automation & Test in Europe, Grenoble, France, Mar. 14-18, 2011; IEEE, May 2011, 6 pages.

Chrysos et al., "Reconfiguring the Bioinformatics Computational Spectrum: Challenges and Opportunities of FPGA-Based Bioinformatics Acceleration Platforms," IEEE Design & Test, Oct. 2013, 31(1):62-73.

CN Office Action in Chinese Appln. No. 201780006359.1, mailed on Jul. 30, 2021, 37 pages (with English translation).

(56) References Cited

OTHER PUBLICATIONS

CN Office Action in Chinese Appln. No. 201780035840.3, mailed on Aug. 9, 2023, 4 pages (with English translation).
CN Office Action in Chinese Appln. No. 201780035840.3, mailed on Sep. 5, 2022, 12 pages (with English translation).
CN Office Action in Chinese Appln. No. 202210534739.5, mailed on Jul. 11, 2024, 17 pages (with English translation).
Derrien et al., "Fast Computation and Applications of Genome Mappability," PLOS One, Jan. 2012, retrieved on May 25, 2016, retrieved from URL <https://journals.plos.org/plosone/article?id=10.1371/journal.pone.0030377>, 15 pages.
Derrien et al., "Hardware acceleration of HMMER on FPGAs," Journal of Signal Processing Systems, Jan. 2010, 58(1):53-67.
Deutsch, "Quantum theory, the Church-Turing principle and the universal quantum computer," Proceedings of the Royal Society of London A 400, 1985, pp. 97-117.
Dilthey et al., "Improved genome inference in the MHC using a population reference graph," Nature Genetics, Apr. 2015, 47:682-688.
Doddavula et al., "Implementation of a Scalable Next Generation Sequencing Business Cloud Platform—An Experience Report," Paper, Presented at the 2011 IEEE 4th International Conference on Cloud Computing, Washington D.C., USA, Jul. 4-9, 2011; IEEE, Sep. 2011, pp. 598-605.
Dydel et al., "Large Scale Protein Sequence Alignment Using FPGA Reprogrammable Logic Devices," Lecture Notes, Presented at the 4th International Conference of Field Programmable Logic and Application (FPL), Leuven, Belgium, Aug. 30-Sep. 1, 2004, 3203:23-32.
EP European Search Report in European Appln. No. 14740602.9, dated Mar. 15, 2022, 14 pages.
EP European Search Report in European Appln. No. 19199685.9, dated Jan. 3, 2020, 13 pages.
EP Extended European Search Report in European Appln. No. 24162764.5, mailed on Jun. 17, 2024, 9 pages A43.
EP Extended Search Report in European Appln. No. 21179125.6, mailed on Nov. 29, 2021, 9 pages.
EP Office Action in European Appln. No. 17731690, mailed on Jan. 4, 2020, 19 pages.
EP Office Action in European Appln. No. 17731690.8, mailed on Apr. 1, 2020, 19 pages.
EP Office Action in European Appln. No. 21179125.6, mailed on Dec. 10, 2024, 6 pages.
EP Office Action in European Appln. No. 21190670.6, mailed on Feb. 1, 2023, 8 pages.
Eusse et al., "A Protein Sequence Analysis Hardwar Accelerator Based on Divergences," International Journal of Reconfigurable Computing, Jan. 2012, 2012:2017378, 19 pages.
Faes et al., "Scalable Hardware Accelerator for Comparing DNA and Protein Sequences," Paper, Presented at the InfoScale '06: Proceedings of the 1st International Conference on Scalable Information Systems, Hong Kong, China, May 30-Jun. 1, 2006, 6 pages.
Fagin et al., "FPGA and Rapid Prototyping Technology Use in a Special Purpose Computer for Molecular Genetics," 1992, Thayer School of Engineering, retrieved on Jan. 11, 2017, retrieved from URL <http://www.faginfamily.net/barry/Papers/ICCD92.htm>, 6 pages.
Fernandez et al., "Exploration of Short Reads Genome Mapping in Hardwares," Paper, Prasented at the 20th International Conference on Field Programmable Logic and Applications (FPL), Milano, Italy, Aug. 31-Sep. 2, 2010, 4 pages.
Fernandez et al., "Multithreaded FPGA Acceleration of DNA Sequence Mapping," Paper, Presented at the 2012 IEEE Conference on High Performance Extreme Computing, Waltham, Massachusets, Sep. 10-12, 2012; IEEE, Jan. 2013, 6 pages.
Fernandez et al., "Multithreaded FPGA Acceleration of DNA Sequence Mapping," PowerPoint Presentation, UC Riverside, Department of Computer Science and Engineering Jacquard Computing, 2012, 20 pages.
Ferraz et al., "Evaluating Optimization Strategies for HMMer Acceleration on GPU," Paper, Presented at the 2013 International Conference on Parallel and Distributed Systems, Seoul, South Korea, Dec. 15-18, 2013; IEEE, May 2014, pp. 59-68.
Feynman, "Simulating Physics with Computers," International Journal of Theoretical Physics, 1982, 21(6/7):467-488.
Fromer et al., "Discovery and statistical genotyping of copy-number variation from whole-exome sequencing depth," The American Journal of Human Genetics, Oct. 2012, 91(4):597-607.
Giraldo et al., "A HMMER hardware accelerator using divergences," Paper, Presented at the 2010 Design, Automation & Test in Europe Conference & Exhibition (Date 2010), Dresden, Germany, Mar. 8-12, 2010; IEEE, Apr. 2010, pp. 405-410.
github.com [online], "Spring," Jan. 24, 2020, retrieved on Jan. 16, 2025, retrieved from URL <https://github.com/shubhamchandak94/Spring >, 7 pages.
Grabherr et al., "Genome-wide synteny through highly sensitive sequence alignment: Satsuma," Bioinformatics, May 2010, 26(9):1145-1151.
Guccione et al., "Gene Matching Using JBits," Paper, Presented at the12th International Conference on Field Programmable Logic and Applications, Montpellier, France, Sep. 2-4, 2002; Field-Programmable Logic and Applications, Aug. 2022, 9 pages.
Guo et al., "A Systolic Array-Based FPGA Parallel Architecture for the BLAST Algorithm," International Scholarly Research Notices, Sep. 2012, 2012(1):195658, 13 pages.
Hach et al., "SCALCE: boosting sequence compression algorithms using locally consistent encoding," Bioinformatics, Dec. 2012, 28(23):3051-3057.
Hall, "Short-Read DNA Sequence Alignment with Custom Designed FPGA-based Hardware," B.A., The University of Cambridge, 2007, Thesis for the degree of Master of Science, The University of British Columbia, Nov. 2010, 186 pages.
Hardcastle et al., "baySeq: Empirical Bayesian methods for identifying differential expression in sequence count data," BMC Bioginformatics, Aug. 2010, retrieved on May 25, 2016, retrieved from URL <http://bmcbioinformatics.biomedcentral.com/articles/10.1186/1471-2105-11-422>, 16 pages.
Harris et al., "A banded Smith-Waterman FPGA accelerator for mercury BLASTP", Paper, Presented at the 2007 International Conference on Field Programmable Logic and Applications, Amsterdam, Netherlands, Aug. 27-29, 2007; IEEE, Nov. 2007, 5 pages.
Hasan et al., "An Overview of Hardware-Based Acceleration of Biological Sequence Alignment," Computational Biology and Applied Bioinformatics, Sep. 2011, pp. 187-202.
Herbordt et al., "Single Pass Streaming BLAST on FPGAs", Parallel Comput. Nov. 2007, 33(10-11):741-756, NIH Public Access Author Manuscript, 25 pages.
Herbordt et al., "Single Pass, BLAST-like, Approximate String Matching of FPGAs," Boston University, 2006, 19 pages.
Hoang et al., "FPGA Implementation of Systolic Sequence Alignment," Paper, Presented at the International Conference on Field-Programmable Logic and Applications, Vienna, Austria, Aug. 31-Sep. 1992, 4 pages.
Hoang, "A Systolic Array for the Sequence Alignment Problem," Brown University, Apr. 1992, 25 pages.
Hoang, "Searching Genetic Databases on Splash 2," Paper, Presented at the Proceedings IEEE Workshop on FPGAs for Custom Computing Machines, Napa, California, Apr. 5-7, 1993; IEEE, published online Aug. 2002, pp. 185-191.
Holt et al., "MAKER2: an annotation pipeline and genome-database management tool for second-generation genome projects," BMC Bioinformatics, Dec. 2011, 12(1):1-4.
Homer et al., "BFAST: An Alignment Tool for Large Scale Genome Resequencing," PLOS One, Nov. 2009, retrieved on May 25, 2016, retrieved from URL <https://journals.plos.org/plosone/article?id=10.1371/journal.pone.0007767>, 11 pages.
Huang et al., "Hardware Acceleration of the Pair-HMM Algorithm for DNA Variant Calling," Proceedings of the 2017 ACM/SIGDA International Symposium on Field-Programmable Gate Arrays, Monterey, California, Feb. 22-24, 2017, pp. 275-284.
Hughey, "Parallel Hardware for Sequence Comparison and Alignment," Cabios, 1996, 12(6):473-479.
Hwang et al., "The mechanism of personalized service recommendation for the academic field," Paper, Presented at the 2017 4th

(56) References Cited

OTHER PUBLICATIONS

International Conference on Computer Applications and Information Processing Technology (CAIPT), Kuta Bali, Indonesia, Aug. 8-10, 2017; IEEE, Mar. 2018, 5 pages.

IL Office Action in Israeli Appln. No. 263528, mailed on Jun. 22, 2023, 6 pages (with English translation).

IN Office Action in Indian Appln. No. 201827043970, mailed on Sep. 9, 2021, 6 pages (with English translation).

IN Office Action in Indian Appln. No. 202218018463, mailed on Sep. 26, 2024, 7 pages.

IN Office Action in Indian Appln. No. 202218018469, mailed on Sep. 26, 2024, 8 pages.

Iqbal et al., "De novo assembly and genotyping of variants using colored de Bruijn graphs," Nature Genetics, Feb. 2012, 44(2):226, 17 pages.

Isa et al., "A novel efficient FPGA architecture for HMMER acceleration," Paper, Presented at the 2012 International Conference on Reconfigurable Computing and FPGAs, Cancun, Mexico, Dec. 5-7, 2012; IEEE, Jan. 2013, 6 pages.

Jacob et al. "FPGA-Accelerated seed generation in Mercury BLASTP," Paper, Presented at the 15th Annual IEEE Symposium on Field-Programmable Custom Computing Machines (FCCM 2007), Napa, California, Apr. 23-25, 2007; IEEE, Sep. 2007, 10 pages.

Jacob et al., "Preliminary Results in Accelerating Profile HMM Search on FPGAs," Paper, Presented at the Sixth IEEE International Workshop on High Performance Computational Biology, Long Beach, California, Mar. 26-30, 2007; IEEE, Jun. 2007, 9 pages.

Jiang et al., "An efficient parallel implementation of the hidden markov methods for genomic sequence—search on a massively parallel system," IEEE Transactions on Parallel and Distributed Systems, Dec. 2007, 19(1):15-23.

JP Office Action in Japanese Appln. No. 2018-555440, dated Jan. 31, 2022, 4 pages (with English translation).

JP Notice of Allowance in Japanese Appln. No. 2018-555440, mailed on Jun. 12, 2023, 6 pages (with English translation).

JP Office Action in Japanese Appln. No. 2018-564374, mailed on Oct. 4, 2021, 7 pages (with English translation).

JP Office Action in Japanese Appln. No. 2022-046805, mailed on Jun. 5, 2023, 18 pages (with English translation).

JP Office Action in Japanese Appln. No. 2022-089149, mailed on Jun. 19, 2023, 9 pages (with English translation).

JP Office Action in Japanese Appln. No. 2023-196840, mailed on Sep. 9, 2024, 6 pages (with English translation).

Kasap et al., "Design and Implementation of an FPGA-based Core for Gapped BLAST Sequence Alignment with the Two-Hit Method", Engineering Letters, Aug. 2008, 16(3):1-10.

Kim et al., "A review on Sequence Alignment Algorithms for Short Reads Based on Next-Generation Sequencing," IEEE Access, Oct. 2020,8:189811-189822.

KR Office Action in Korean Appln. No. 10-2024-7005077, mailed on Dec. 12, 2024, 19 pages (with English translation).

Lancaster et al., "Acceleration of Ungapped Extension in Mercury BLAST," Proceedings of the 7th Workshop on Media and Streaming Processors, Washington University, Nov. 2005, 9 pages.

Lancaster, "Design and Evaluation of a BLAST Ungapped Extension Accelerator, Master's Thesis," Thesis for the degree of Master of Science, Washington University, May 2006, 79 pages.

Langmead et al., "Searching for SNPs with cloud computing," Genome Biology, Nov. 2009, 10:R134, 10 pages.

Langmead, "ADS1: Variations on k-mer indexes", Jun. 18, 2015, retrieved Jul. 13, 2023, retrieved from URL <https://www.youtube.com/watch?v=My_sw_Rf_4U>, 1 page.

Lavenier, "SAMBA: Systolic Accelerator for Molecular Biological Applications," Research Report, RR-2845, INRIA, Mar. 1996, 22 pages.

Lee et al., "Clinical exome sequencing for genetic identification of rare Mendelian disorders," Jama, Nov. 2014, 312(18):1880-1887.

Lemoine et al., "High Speed Pattern Matching in Genetic Data Base with Reconfigurable Hardware," Paper, Presented at the Proceed-ings of the International Conference of Intelligent Systems for Molecular Biology, France, 1994, 2:269-275.

Li et al., "A survey of sequence alignment algorithms for next-generation sequencing," Briefings in Bioinformatics, Sep. 2010, 11(5):473-483.

Li et al., "160-fold acceleration of the Smith-Waterman algorithm using a field programmable gate array (FPGA)," BMC Bioinformatics, Jun. 2007, 8:185, 7 pages.

Liu et al., "An FPGA-Based Web Server for High Performance Biological Sequence Alignment," Paper, Presented at the 2009 NASA/ESA Conference on Adaptive Hardware and Systems, San Francisco, California, Jul. 29-Aug. 1, 2009; IEEE, Nov. 2009, pp. 361-368.

Liu et al., "Bisulfite-free direct detection of 5-methylcytosine and 5-hydroxymethylcytosine at base resolution," Nature Biotechnology, Apr. 2019, 37(4):424-429.

Lloyd et al., "Hardware Accelerated Sequence Alignment with Traceback," International Journal of Reconfigurable Computing, 2009, 2009:762362, 11 pages.

Lopresti, "Rapid Implementation of a Genetic Sequence Comparator Using Field-Programmable Logic Arrays," Advanced Research in VLSI, 1991, pp. 138-152.

Luethy et al., "Hardware and software systems for accelerating common bioinformatics sequence analysis algorithms," Drug Discovery Today: Biosilico, Jan. 2004, 2(1):12-17.

Madhavan et al., "Race Logic: A Hardware Acceleration for Dynamic Programming Algorithms," Paper, Presented at the 2014 ACM/IEEE 41st International Symposium on Computer Architecture (ISCA), Minneapolis, Minnesota, Jun. 14-18, 2014; IEEE, Jul. 2014, 12 pages.

Mahram, "FPGA Acceleration of Sequence Analysis Tools in Bioinformatics," Dissertation for the degree of Doctor of Philosophy, Boston University, College of Engineering, 2013, 180 pages.

Mandelker et al., "Navigating highly homologous genes in a molecular diagnostic setting: a resource for clinical next-generation sequencing," Genetics in Medicine, Dec. 2016, 18(12):1282-1289.

Maxfield, "Impulse achieves 16X speed-up of genome analysis on $2,500 FPGA module," EE Times, Jun. 15, 2012, retrieved on Mar. 29, 2016, retrieved from URL <http://www.eetimes.com/documentasp?docid=1317288&print=yes>, 4 pages.

McKenna et al., "The Genome Analysis Toolkit: a MapReduce framework for analyzing next-generation DNA sequencing data," Genome Research, Sep. 2010, 20(9):1297-1303.

Mikami et al., "Efficient FPGA-based Hardware Algorithms for Approximate String Matching," Paper, Presented at the 23rd International Technical Conference on Circuits/Systems, Computers and Communications (ITC-CSCC), Yamaguchi, Japan, Jul. 6-9, 2008, pp. 201-204.

Miller et al., "A 26-hour system of highly sensitive whole genome sequencing for emergency management of genetic diseases," Genome Medicine, Sep. 2015, 7:100, 16 pages.

Mishra, "Gappy TotalReCaller for RNASeq Base-Calling and Mapping," bioRxiv:000489, Jan. 2013, 10 pages.

Moritz et al., "Implementation of a Parallel Algorithm for Protein Pairwise Alignment Using Reconfigurable Computing," Paper, Presented at the 2006 IEEE International Conference on Reconfigurable Computing and FPGA's (ReConFig 2006), San Luis Potosi, Mexico, Sep. 20-22, 2006; IEEE, Feb. 2007, 7 pages.

Muriki et al., "RC-BLAST: Towards a Portable, Cost-Effective Open Source Hardware Implementation," Paper, Presented at the 19th IEEE International Parallel and Distributed Processing Symposium, Denver, Colorado, Apr. 4-8, 2005; IEEE, Apr. 2005, 8 pages.

MX Office Action in Mexican Appln. No. MX/a/2018/008527, mailed on May 25, 2023, 9 pages (with English translation).

MY Office Action in Malaysian Appln. No. PI 2018702376, mailed on Jun. 17, 2022, 3 pages.

Nagasaki et al., "DDBJ read annotation pipeline: a cloud computing-based pipeline for high-throughput analysis of next-generation sequencing data," DNA Research, Aug. 2013, 20(4):383-90.

Nalbantoglu et al., "Compression of Next Generation Sequencing Data," DCC, Apr. 2015, 10 pages.

(56)　　　　References Cited

OTHER PUBLICATIONS

Nawaz et al., "A Parallel FPGA Design of the Smith-Waterman Traceback," Paper, Presented at the 2010 International Conference on Field-Programmable Technology, Beijing, China, Dec. 8-10, 2010; IEEE, Jan. 2011, 6 pages.

Nawaz et al., "Fast Smith-Waterman hardware implementation," Paper, Presented at the 2010 IEEE International Symposium on Parallel & Distributed Processing, Workshops and Phd Forum (IPDPSW), Atlanta, Georgia, Apr. 19-23, 2010; IEEE, May 2010, 4 pages.

Nelson et al., "Shepard: A Fast Exact Match Short Read Aligner," Paper, Presented at the Tenth ACM/IEEE International Conference on Formal Methods and Models for Codesign (Memcode2012), Arlington, Virginia, Jul. 16-17, 2012; IEEE, Sep. 2012, 4 pages.

NZ Office Action in New Zealand Appln. No. 784186, mailed on Jun. 29, 2023, 3 pages.

NZ Office Action in New Zealand Appln. No. 784189, mailed on Feb. 13, 2024, 7 pages.

NZ Office Action in New Zealand Appln. No. 784189, mailed on Jun. 27, 2023, 3 pages.

NZ Office Action in New Zealand Appln. No. 789137, mailed on Mar. 5, 2024, 2 pages.

NZ Office Action in New Zealand Appln. No. 789138, mailed on Mar. 13, 2024, 2 pages.

NZ Office Action in Russian Appln. No. 743311, mailed on Jun. 21, 2023, 3 pages.

NZ Office Action in Russian Appln. No. 748612, mailed on Dec. 15, 2023, 3 pages.

Oliver et al., "High performance database searching with HMMer on FPGAs," Paper, Presented at the 2007 IEEE International Parallel and Distributed Processing Symposium, Long Beach, California, Mar. 26-30, 2007; IEEE, Jun. 2007, 7 pages.

Oliver et al., "Multiple Sequence Alignment on an FPGA," Paper, Presented at the 11th International Conference on Parallel and Distributed Systems (ICPADS'05), Fukuoka, Japan, Jul. 20-22, 2005; IEEE, Nov. 2005, 5 pages.

Oliver et al., "Using Reconfigurable Hardware to Accelerate Multiple Sequence Alignment with ClustalW," BioInformatics, May 2005, 21(162):3431-3432.

Oliver et al., "A Reconfigurable Computing System Based on a Cache-Coherent Fabric," Paper, Presented at the 2011 International Conference on Reconfigurable Computing and FPGAs, Cancun, Mexico, Nov. 30-Dec. 2, 2011; IEEE, Jan. 2012, 6 pages.

Oliver et al., "Integrating FPGA acceleration into HMMer," Parallel Computing, Sep. 2008, 34:681-691.

Oliver, "Hyper Customized Processors for Bio-Sequence Database Scanning on FPGAs," Paper, Presented at the FPGA '05: Proceedings of the 2005 ACM/SIGDA 13th International Symposium on Field-Programmable Gate Arrays, Monterey, California, Feb. 20-22, 2005; Association for Computing Machinery, Feb. 2005, pp. 229-237.

Olson et al., "Hardware Acceleration of Short Read Mapping," Paper, Presented at the 2012 IEEE 20th International Symposium on Field-Programmable Custom Computing Machines, Toronto, Canada, Apr. 29-May 1, 2012; IEEE, Jul. 2012, 8 pages.

Olson, "An FPGA Acceleration of Short Read Human Genome Mapping," thesis for the degree of Master of Science in Electrical Engineering, University of Washington, 2011, 103 pages.

PCT International Preliminary Report on Patentability in International Appln. No. PCT/US2023/063661, mailed on Sep. 19, 2024, 11 pages.

PCT International Search Report and Written Opinion in International Appln. No. PCT/US2016/020480, mailed on May 17, 2016, 6 pages.

PCT International Search Report and Written Opinion in International Appln. No. PCT/US2016/026796, mailed on Jul. 18, 2016, 8 pages.

PCT International Search Report and Written Opinion in International Appln. No. PCT/US2016/040842, mailed on Oct. 4, 2016, 10 pages.

PCT International Search Report and Written Opinion in International Appln. No. PCT/US2016/18765, mailed on May 6, 2016, 9 pages.

PCT International Search Report and Written Opinion in International Appln. No. PCT/US2017/013057, mailed on Apr. 11, 2017, 10 pages.

PCT International Search Report and Written Opinion in International Appln. No. PCT/US2017/036424, mailed on Sep. 12, 2017, 12 pages.

PCT International Search Report and Written Opinion in International Appln. No. PCT/US2017/040385, mailed on Oct. 27, 2017, 15 pages.

PCT International Search Report and Written Opinion in International Appln. No. PCT/US2017/058890, mailed on Feb. 23, 2018, 16 pages.

PCT International Search Report and Written Opinion in International Appln. No. PCT/US2021/058364, mailed on Feb. 23, 2022, 19 pages.

PCT International Search Report and Written Opinion in International Appln. No. PCT/US2023/063661, mailed on Jun. 6, 2023, 18 pages.

PCT International Search Report and Written Opinion in International Appln. No. PCT/US2024/031054, mailed on Nov. 12, 2024, 9 pages.

PCT International Search Report and Written Opinion in International Appln. No. PCT/US2024/031062, mailed on Aug. 22, 2024, 11 pages.

PCT International Search Report in International Appln. No. PCT/US2014/012144, mailed on Jun. 18, 2014, 2 pages.

Peltenburg et al., "Maximizing systolic array efficiency to accelerate the PairHMM Forward Algorithm," Paper, Presented at the 2016 IEEE International Conference on Bioinformatics and Biomedicine (BIBMJ, IEEE), Shenzhen, China, Dec. 15-18, 2016; IEEE, Jan. 2017, pp. 758-762.

Raphael et al., "A novel method for multiple alignment of sequences with repeated and shuffled elements," Genome Research, Nov. 2004, 14(11):2336-2346.

Ren et al., "FPGA acceleration of the pair-HMMs forward algorithm for DNA sequence analysis," Paper, Presented at the 2015 IEEE International Conference on Bioinformatics and Biomedicine (BIBM), Washington D.C., USA, Nov. 9-12, 2015; IEEE, Dec. 2015, 6 pages.

Rimmer et al., "Integrating mapping-, assembly-and haplotype-based approaches for calling variants in clinical sequencing applications," Nature Genetics, Aug. 2014, 46(8):912-918.

Roy et al., "Turtle: Identifying frequent k-mers with cache-efficient algorithms," Bioinformatics, Jul. 2014, 30(14):1950-1957.

RU Office Action in Russian Appln. No. 2021118824, mailed on Oct. 17, 2022, 21 pages (with English translation).

RU Office Action in Russian Appln. No. 2021134292, dated Nov. 23, 2022, 13 pages (with English translation).

Ruffalo et al., "Comparative analysis of algorithms for nextgeneration sequencing read alignment," Bioinformatics, Aug. 2011, 27(20):2790-2796, retrieved on May 25, 2016, retrieved from URL <https://bioinformatics.oxfordjournals.org/content/27/20/2790.full>, 12 pages.

Russell, "TGAC Unleashes DRAGEN to Accelerate Genomics Workflows," HPC Wire, Oct. 28, 2015, retrieved on Apr. 12, 2022, retrieved from URL <https://www.hpcwire.com/2015/10/28/tgac-unleashes-dragen-to-accelerate- genomics-workflows/>, 12 pages.

Sarkar et al., "Network-on-Chip Hardware Accelerators for Biological Sequence Alignment," IEEE Transactions on Computers, Jan. 2010, 59(1):29-41.

Schatz et al., "Cloud Computing and the DNA Data Race," Nature Biotechology, Jul. 2010, 28(7):691-693 (HHS Public Access Author Manuscript).

Schatz et al., "High-throughput sequence alignment using Graphics Processing Units," BMC Bioinformatics, Dec. 2007, retrieved on May 25, 2016, retrieved from URL <http://bmcbioinformatics.biomedcentral.com/articles/10.1186/1471-2105-8-474>, 13 pages.

Schatz, "CloudBurst: highly sensitive read mapping with MapReduce," Bloinformatics, Apr. 2009, 25(11):1363-1369, retrieved on May 25, 2016, retrieved from URL <http:///bioinformatics.oxfordioumals.ora/content/25/11/1363.full>, 14 pages.

(56) References Cited

OTHER PUBLICATIONS

Settle et al., "High-Performance Dynamic Programming on FPGAs with OpenCL," Paper, Presented at the 2013 IEEE High Performance Extreme Computing Conference (HPEC), Waltham, Massachusets, Sep. 10-12, 2013; IEEE, 2013, 6 pages.
SG Office Action in Singaporean Appln. No. 11201805562Q, mailed on Oct. 26, 2022, 5 pages.
SG Office Action in Singaporean Appln. No. 11202200666W, mailed on Feb. 28, 2025, 9 pages.
Sotiriades et al., "FPGA based Architecture for DNA Sequence Comparison and Database Search," Paper, Presented at the Proceedings 20th IEEE International Parallel & Distributed Processing Symposium, Rhodes, Greece, Apr. 25-29, 2006; IEEE, Jun. 2006, 8 pages.
Setiriades et al., "Some Initiai Results on Hardware BLAST acceleration with a Reconfigurable; Architecture," Paper, Presented at the Proceedings 20th IEEE International Parallel & Distributed Processing Symposium, Rhodes, Greece, Apr. 25-29, 2006; IEEE, Jun. 2006, 8 pages.
Sun et al., "Accelerating HMMer on FPGAs using systolic array based architecture," Paper, Presented at the 2009 IEEE International Symposium on Parallel & Distributed Processing, Rome, Italy, May 23-29, 2009; IEEE, Jul. 2009, 8 pages.
Tang et al., "Accelerating Millions of Short Reads Mapping on a Heterogeneous Architecture with FPGA Accelerator," Paper, Presented at the 2012 IEEE 20th International Symposium on Field-Programmable Custom Computing Machines, Toronto, Canada, Apr. 29-May 1, 2012; IEEE, Jul. 2012, pp. 184-187.
TimeLogic, "Accelerated Blast Performance with Tera-Blast: a comparison of FPGA versus GPU and CPU Blast implementations," Technical Note, May 2013, Version 1.0, 5 pages.
Treangen et al., "Gapped extension for local multiple alignment of interspersed DNA repeats," Paper, Presented at the ISBRA International Symposium on Bioinformatics Research and Applications 2008, Atlanta, Georgia, May 6-8, 2008; Bioinformatics Reasearch and Applications, 2008, 4983:74-86.
US Office Action in U.S. Appl. No. 15/048,935, mailed on Sep. 14, 2021, 21 pages.
US Office Action in U.S. Appl. No. 15/616,833, mailed on Apr. 4, 2019, 6 pages.
US Office Action in U.S. Appl. No. 15/643,381, mailed on Jan. 22, 2018, 9 pages.
US Office Action in U.S. Appl. No. 15/907,263, mailed on May 3, 2018, 6 pages.
US Office Action in U.S. Appl. No. 15/915,013, mailed on Oct. 2, 2020, 5 pages.
US Office Action in U.S. Appl. No. 16/120,103, mailed on Oct. 5, 2020, 5 pages.
US Office Action in U.S. Appl. No. 17/165,900, mailed on Dec. 13, 2024, 5 pages.
US Office Action in U.S. Appl. No. 17/165,900, mailed on Jun. 20, 2024, 10 pages.
US Office Action in U.S. Appl. No. 17/520,615, mailed on Feb. 18, 2022, 5 pages.
US Office Action in U.S. Appl. No. 17/974,978, mailed on Mar. 6, 2023, 6 pages.
US Office Action in U.S. Appl. No. 18/117,088, mailed on Dec. 20, 2023, 31 pages.
US Office Action in U.S. Appl. No. 18/117,088, mailed on Sep. 12, 2023, 28 pages.

US Office Action in U.S. Appl. No. 18/117,088, mailed on Sep. 6, 2024, 40 pages.
Van Court et al., "Families of FPGA-Based Algorithms for Approximate String Matching," Paper, Presented at the 15th IEEE International Conference on Application-Specific Systems, Architectures and Processors, Galveston, Texas, Sep. 29, 2024; IEEE, Oct. 2004, 11 pages.
Van Der Auwera et al., "From FastQ data to high confidence variant calls: the Genome Analysis Toolkit best practices pipeline," Current Portocols in Bioinformatics, Oct. 2013, 11(1110):11.10.1-11.0.33 (HHS Public Access Author Manuscript), 27 pages.
Wan et al., "Transformations for the compression of FASTQ quality scores of next-generation sequencing data," Bioinformatics, Mar. 2012, 28(5):628-635.
Wang et al., "Heterogeneous cloud framework for big data genome sequencing," IEEE/ACM Transactions on Computational Biology and Bioinformatics, Sep. 2014, 12(1):166-78.
wikipedia.org [online], "Arithmetic coding," Oct. 29, 2020, retrieved on Feb. 15, 2022, retrieved from URL <https://en.wikipedia.org/w/index.php?title=Arithmetic_coding&oldid=985967562>, 14 pages.
wikipedia.org [online], "CpG site," Jul. 24, 2021, retrieved on Jan. 16, 2025, retrieved from URL <https://en.wikipedia.org/wiki/CpG_site>, 15 pages.
Wilke et al., "A RESTful API for accessing microbial community data for MG-RAST," PLoS Computational Biology, Jan. 8, 2015, 11(1):e1004008, 8 pages.
Wu et al., "Sequence analysis: GMAP: a genomic mapping and alignment program for mRNA and EST sequences," Bioinformatics, Feb. 2005, 21(92005):1859-1875.
Yamaguchi et al., "High Speed Homology Search with FPGAs," Paper, Presented at the Pacific Symposium on Biocomputing, Kauai, Hawaii, Jan. 3-7, 2002, 7:271-282.
Yu et al, "A Smith-Waterman Systolic Cell," Paper, Presented at the International Conference on Field Programmable Logic and Applications, Lisbon, Portugal, Sep. 1-3, 2003; Field Programmable Logic and Application, Jan. 2003, pp. 375-384.
ZA Notice of Acceptance in South African Appln. No. 2022/10297, mailed on Jun. 5, 2023, 2 pages.
Zhang et al., "A Practical Comparison of De Novo Genome Assembly Software Tools for Next-Generation Sequencing Technologies," PLOS One, Mar. 2011, retrieved on May 25, 2016, retrieved from URL <http://joumals.plos.org/plosone/article?id=10.1371/journal.pone.0017915>, 10 pages.
Zhang et al., "Implementation of the Smith-Waterman algorithm on a reconfigurable supercomputing platform," Proceedings of the 1st international workshop on High-performance reconfigurable computing technology and applications: held in conjunction with SC07, Nov. 11, 2007, 39, 19 pages.
Zhang et al., "Joint haplotype phasing and genotype calling of multiple individuals using haplotype informative reads," Bioinformatics, Oct. 2013, 29(19):2427-2434.
IN Office Action in Indian Appln. No. 202217021491, mailed on Mar. 13, 2025, 7 pages.
IN Office Action in Indian Appln. No. 202217021492, mailed on Mar. 14, 2025, 8 pages.
Jones et al. Compression of next-generation sequencing reads aided by highly efficient de nova assembly, Nucleic Acids Research, 2012, vol. 40, No. 22 e171 doi:10.1093/nar/gks754 (9 pages).
Nonfinal Office Action in U.S. Appl. No. 17/642,519, mailed on Dec. 22, 2025, 25 pages.
Hearing Notice in India App. No. 202217021491, mailed on Apr. 12, 2025, 5 pages.

* cited by examiner

CASE 1 : GLOBAL ALIGNMENT, 2 MISMATCH

REFERENCE
SEQUENCE

READ

MISMATCH          MISMATCH

MISMATCH LIST IS: POSITION 12: T, POSITION 21: G
ENCODED AS: <12,T>, <9,G> RESULTING IN ENCODING 51, 38

CASE 2 : GLOBAL ALIGNMENT, MISMATCH LIST REQUIRING "FAKE MISMATCH"

REFERENCE
SEQUENCE

READ

MISMATCH          "FAKE" MISMATCH          MISMATCH
                  63          49

MISMATCH LIST IS: POSITION 22: T, POSITION 134: G
ENCODED AS: <22,T>, <63,G> <49,G> RESULTING IN ENCODING 91,255,198

METHOD FOR THE COMPRESSION OF GENOME SEQUENCE DATA

CLAIM OF PRIORITY

This application is a continuation of and claims priority to U.S. patent application Ser. No. 16/567,211, filed on Sep. 11, 2019, the entire contents of which are hereby incorporated by reference.

TECHNICAL FIELD

The field relates generally to the methods of representation of genome sequencing data produced by a sequencing machine, and more particularly to the computer-implemented methods for the compression of such genome sequencing data. This disclosure provides a reference-based compression method which allows fast compression and decompression while causing no loss of information, and which has a high compression ratio.

BACKGROUND

Next generation sequencing machines now produce huge amounts of sequencing data at an affordable price. Recent systems produce in a single run of 36 h more than 6 billion 150-nucleotide long sequences, enough for the sequencing of 20 whole human genomes. This opens many new perspectives for the diagnostic of genetic diseases and for the development of personalized medicine, aiming to adapt treatment based on people genomic specificities.

However, this also comes with new challenges, in particular the cost related to the storage of huge amounts of data. The most used file format for raw (unaligned) sequence data is the FASTQ format, holding sequence data (string of A, C, T, G nucleotides, also called read), quality values (probabilities that the sequencing platform made a sequencing error for each nucleotide) and sequence names. This is a plain ASCII text file, usually compressed with the general purpose text compression scheme LZ (Lempel-Ziv scheme, implemented in the gzip software). However, the use of such compression methods comes with several issues:

low compression ratio because the redundancy of the data is not fully used slow compression and decompression There also exists compression methods specialized in FASTQ encoding, divided in reference or non reference-based methods. However, none of them are fully satisfying, since a) the reference-based methods have good compression ratios but are slow, b) the non reference-based methods are faster but have lower compression ratios. An example of such a non reference-based method is provided by the software SPRING, which is a reference-free compressor for FASTQ files (worldwide web address: github.com/shubhamchandak94/SPRING). However, the compression method provided by the software SPRING has a low compression ratio.

Among the reference-based compression methods, some methods that use sequence alignments and are aimed to be faster with good compression ratios have been proposed. However, such methods suffer from several problems, notably a major issue is that they are not completely lossless. Such a known reference-based compression method is for example described in the patent document WO 2018/068829 A1. In the described method, after having been aligned to one or more reference sequences, the sequences of nucleotides are classified according to matching accuracy degrees (thereby creating classes of aligned reads), and are then coded as a multiplicity of layers of syntax elements, using different source models and entropy coders for each layer in which the data is partitioned. The classes of data are thus encoded separately and are structured in different layers of syntax elements, each layer comprising descriptors which univocally represent the classified and aligned reads of said layer. The method is intended to obtain distinct information sources with reduced information entropy, thereby allowing an increase in compression performance as well as a selective access to specific classes of compressed data. However, such a compression method reorders the reads in an order that is different from that obtained at the end of the read alignment step (i.e. the reads are reordered according to their classes). Some information is then lost in the compression process, notably the initial sequence ordering. Hence the reproducibility of some analysis results can be affected, because some downstream analysis software can be dependent on the order of the reads. Besides, decompressing the data in an order that is different from the initial order of the reads makes it much more difficult to check that the uncompressed file is identical to the initial file. Furthermore, such a compression method is relatively slow, especially when compared to the non reference-based compression methods of the state of the art.

SUMMARY

The features of the independent claims below solve the problem of existing prior art solutions by providing a method for the compression of genome sequence data. In one aspect, a computer-implemented method for the compression of genome sequence data produced by a sequencing machine, said genome sequence data comprising reads of sequences of nucleotides or bases that have been aligned to a reference sequence, thereby creating aligned reads, said aligned reads being stored as a list of reads in an initial file, comprises the steps of:

for each aligned read, determining whether said read is perfectly or imperfectly mapped with said reference sequence or whether said read is unmapped with said reference sequence, encoding the reads according to said determination, wherein the reads that are determined to be perfectly mapped are encoded according to a first encoding process and the reads that are determined to be unmapped are encoded according to a second encoding process, wherein the determining step comprises comparing, for each imperfectly mapped read, the number of mismatches between said read and said reference sequence with a threshold value, wherein, in the encoding step, the reads that are determined to be imperfectly mapped are encoded according to the second encoding process or to a third encoding process, the imperfectly mapped reads being encoded according to the second encoding process when said number of mismatches is greater than the threshold value, the imperfectly mapped reads being encoded according to the third encoding process when said number of mismatches is lower than the threshold value, wherein, in said second encoding process, each nucleotide or base of the read is individually encoded, wherein said first and third encoding processes comprise distinct sets of descriptors, each set of descriptors univocally representing the reads associated to the corresponding encoding process, each of said first and third encoding processes being a reduced information source entropy encoding process.

The invention overcomes the disadvantages of prior compression methods by allowing fast compression and decompression while causing no loss of information, and providing a high compression ratio. More particularly, the invention focuses on encoding the most frequent cases in the most compact way, even if this means adopting degraded encoding modes for the rare least frequent cases. This leads to a huge increase in compression performance. Moreover, due to the genomic information representation format that is used in the invention, the compression performed by the method according to the invention is faster. Last but not least, the method according to the invention keeps the initial order of the reads as such and does not reorder the reads according to their classes. Consequently, no information is lost during the process, which enables an easier downstream analysis as well as efficient conformity checks after the decompression step.

These and other features and advantages of the present invention will become more apparent from the accompanying drawings and the following detailed description.

DETAILED DESCRIPTION

Figure 1:
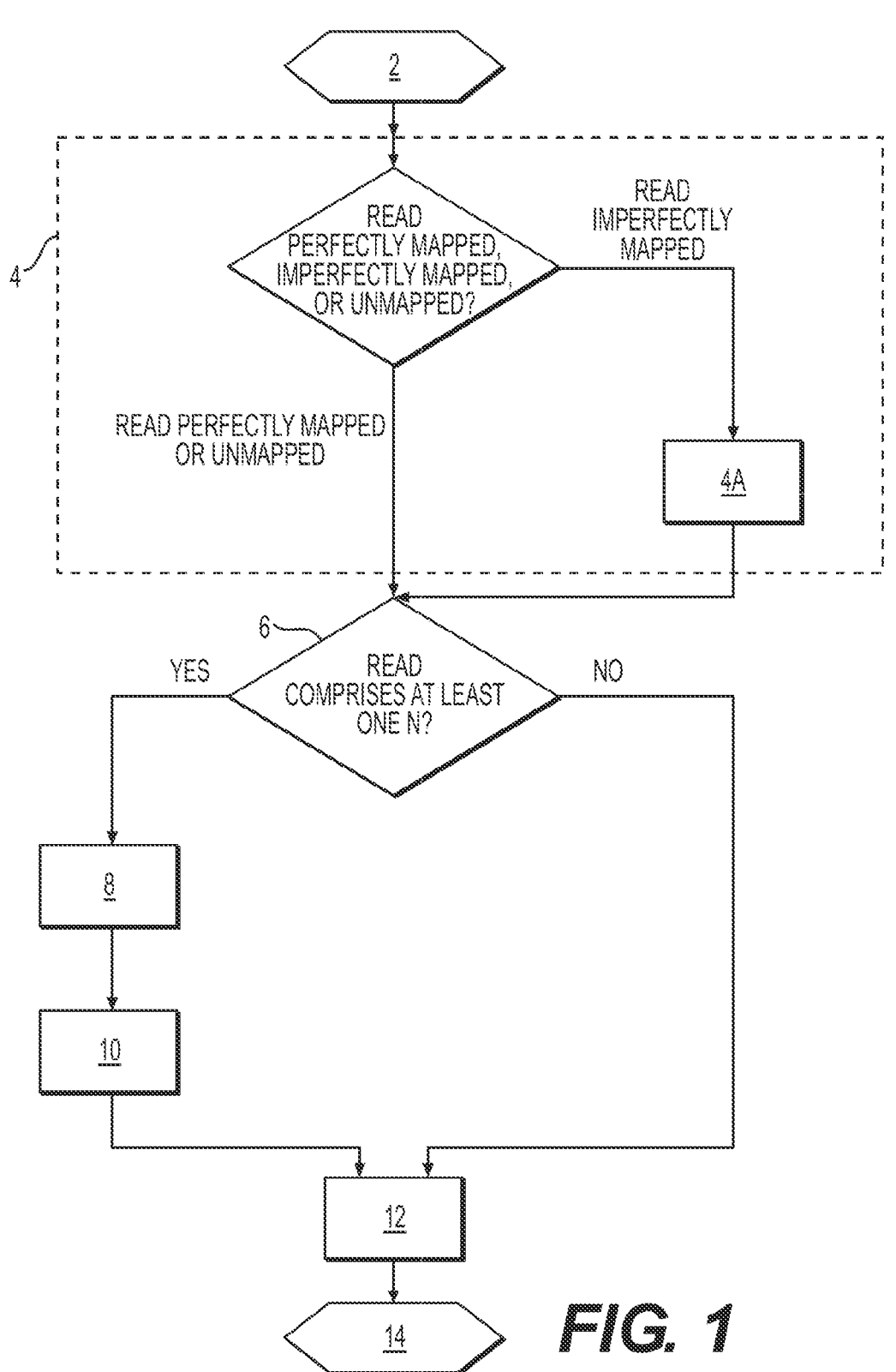
FIG. 1 is a is a flow diagram showing the steps of the compression method according to the invention.

The genomic sequences referred to in this invention include, for example, and not as a limitation, nucleotide sequences, Deoxyribonucleic acid (DNA) sequences, Ribonucleic acid (RNA), and amino acid sequences. Although the description herein is in considerable detail with respect to genomic information in the form of a nucleotide sequence, it will be understood that the compression method according to the invention can be implemented for other genomic sequences as well, albeit with a few variations, as will be understood by a person skilled in the art.

Genome sequencing information is generated by sequencing machines in the form of sequences of nucleotides (or, more generally, bases) represented by strings of letters from a defined vocabulary. The smallest vocabulary is represented by five symbols: {A, C, G, T, N} representing the 4 types of nucleotides present in DNA namely Adenine, Cytosine, Guanine, and Thymine. In RNA Thymine is replaced by Uracil (U). N indicates that the sequencing machine was not able to call any base and so the real nature of the position is undetermined.

The nucleotide sequences produced by sequencing machines are called "reads". Sequence reads can be between a few dozens to several thousand nucleotides long. Some technologies produce sequence reads in pairs where one read is from one DNA strand and the second is from the other strand. Throughout this disclosure, a "reference sequence" is any sequence on which the nucleotide or base sequences produced by sequencing machines are aligned/mapped. One example of such a reference sequence could actually be a reference genome, i.e. a sequence assembled by scientists as a representative example of a species' set of genes. However, a reference sequence could also consist of a synthetic sequence conceived to merely improve the compressibility of the reads in view of their further processing. Sequencing machines can introduce errors in the sequence reads, and notably a use of a wrong symbol (i.e. representing a different nucleic acid) to represent the nucleic acid or base actually present in the sequenced sample; this is usually called a substitution error or a "mismatch".

The invention is a reference-based compression method that receives reads of sequences of nucleotides or bases as inputs, such reads having been previously aligned to a reference sequence, thereby creating aligned reads. The aligned reads are then stored as a list of reads in an initial file. The way to align reads and to store them once aligned in an initial file is not critical to the invention and is not the purpose of the present disclosure. Each read is then encoded as a position on the reference sequence and a list of differences with said reference sequence. Each read can then be reconstructed from the alignment encoded information and the reference sequence, by a proper decompression software configured according to the present invention.

Preferably, the alignment software which processes the reads and aligns them to the reference sequence prior to providing them as inputs to the compression software and apparatus does not take into account certain types of errors introduced in the sequence reads, such as for example insertion errors or deletion errors. An insertion error consists in the insertion in one sequence read of one ore more additional symbols that no not refer to any actually present nucleic acid. A deletion error consists in the deletion from one sequence read of one or more symbols that represent nucleic acids that are actually present in the sequenced sample. More precisely, in case of an insertion error or a deletion error in a given sequence read, the alignment software will then consider the resulting erroneous nucleic acids as substitution errors, also called "mismatches". This preferential choice for the alignment software configuration allows faster subsequent coding, providing notably a better compromise between speed and compression ratio.

For each read, the alignment software provides a corresponding read record to the compression software and apparatus. Each read record contains at least the following information: the absolute starting position of the aligned read with respect to the reference sequence, the length of the read, the type of alignment of the read, the number of mismatches identified in the read, and the relative position of said possible mismatches in the read (where appropriate).

The compression method according to the present invention will now be described with reference to FIG. 1. The method is for example performed by an apparatus 20 shown in FIG. 2. The apparatus comprises at least one processor 22 and one memory 24 operatively coupled to the processor 22 to form a computing device. The memory 24 may store a computer program code or software 26 comprising computer executable instructions which, when executed by the processor 22, cause the processor 22 to perform operations comprising the steps of the compression method according to the invention.

The initial file in which the aligned reads are stored as a list of reads is for example stored in a memory of the apparatus 20. Returning to FIG. 1, the method preferably comprises an initial step 2 wherein the initial list of aligned reads is divided into blocks of reads. Typically, the list of aligned reads is divided into blocks of 50 000 reads, this specific value not being construed as limiting the scope of the present invention which can be applied in the same way with other values. Preferably, the blocks of reads have the same block size. Each block of reads begins with a header containing information needed to decode the block, such as for example the size in bytes of the content of the block, and/or an identifier of the block or its content and/or the number of reads contained in the block. This allows support for the concatenation of compressed file, as well as streaming capabilities (each block of reads containing all the information needed to decode the reads of the block). Besides, since the compression method can then be performed block after block, this also allows multi thread processing on the blocks of reads, thereby allowing parallelization and some resulting gain in processing time. If all the reads of a given block have the same length, the read length is also stored in the header, otherwise a list of each read length is stored explicitly during the compression method.

Each read record contains information about the type of alignment of the read. Typically, two main types of alignment can be identified: perfect alignment and imperfect alignment, plus an additional type corresponding to an "unmapped" read. "Imperfect alignment" means that the read contains at least one mismatch other than a N, while at least a portion of the read matches a portion of the reference sequence (according to this definition, an imperfectly mapped read may contain one or more N, provided it also contains one or more other mismatches). In an exemplary embodiment, each read record starts with the following bit flags, each bit flag having one value among two possible values:

a first bit flag indicative of a forward or reverse orientation versus the reference sequence, a second bit flag indicative of a perfect alignment or not, a third bit flag indicative of whether the read contains at least one N, a fourth bit flag indicative of whether the position information is encoded on 16 bits or 32 bits.

The following steps 4-12 are performed block of reads after block of reads, and read after read within the blocks.

The method comprises a next step 4 of determining, for each aligned read, whether said read is perfectly or imperfectly mapped with the reference sequence, or whether said read is unmapped with the reference sequence. This determining step 4 comprises, for each imperfectly mapped read, comparing 4a the number of mismatches between said read and the reference sequence with a threshold value. In a preferred embodiment, though not to be construed as limiting the scope of the present invention, said threshold value is equal to 31. This specific value has been purposely chosen so as to provide the best possible compromise for storing the number of mismatches in a sufficiently compact manner, as will be better understood later with regard to step 12. Indeed, it has been statistically observed that in a vast majority of the cases, the imperfectly mapped reads have less than 31 mismatches. The principle lying behind that choice consists in encoding in the most compact way the most frequent cases, leave to have some very few degraded cases. If a read is determined to be imperfectly mapped with a number of mismatches lower than the threshold value, the determining step 4 comprises a further determination as to whether the read is globally or locally mapped with the reference sequence. A "globally mapped read" is an imperfectly mapped read whose whole sequence, comprising the beginning and the end of the read, is imperfectly mapped with the reference sequence. A "locally mapped read" is an imperfectly mapped read containing a segment of nucleotides or bases that is imperfectly mapped with the reference sequence. Said segment of nucleotides or bases thus corresponds to a portion of the initial read.

Preferably, the method further comprises a step 6 of determining, for each aligned read, whether said read comprises at least one N, i.e. whether said read comprises at least one mismatch corresponding to a case in which the sequencing machine was not able to call any base or nucleotide. The method then comprises, for each read comprising at least one N, a step 8 of determining the number of such N mismatches and a step 10 of comparing said number of N mismatches with a reference threshold value. In a preferred embodiment, though not to be construed as limiting the scope of the present invention, said reference threshold value is equal to 31.

Whatever the outcome of the determination step 4, the method comprises a next step 12 of encoding the reads according to said determination at least. More precisely, the reads that are determined to be perfectly mapped with the reference sequence, whether they comprise no N or has a number of N lower than the reference threshold value, are encoded according to a first encoding process. The reads that are determined to be unmapped or the reads that are determined to be perfectly mapped but with a number of N greater than the reference threshold value are encoded according to a second encoding process in which each nucleotide or base is individually encoded, regardless of whether said nucleotide or base is aligned or not. The reads that are determined to be imperfectly mapped are encoded according to the second encoding process or to a third encoding process. More precisely, the reads that are determined to be imperfectly mapped with a number of mismatches greater than the threshold value are encoded according to the second encoding process. If a read is determined to be imperfectly mapped with a number of mismatches lower than the threshold value, if said read comprises no N or has a number of N lower than the reference threshold value, then said read is encoded according to the third encoding process. If not, i.e. if the read has a number of N greater than the reference threshold value, then said read is encoded according to the second encoding process.

Whether a given read has been determined as being perfectly mapped, imperfectly mapped or unmapped, if said read comprises at least one N but has a number of N lower than the reference threshold value, the encoding step 12 comprises encoding a list of positions along the reference sequence, said positions corresponding to the positions of the N in the reference sequence. The list of positions is then stored in a memory of a computing device, said device implementing the compression method. If a read comprises at least one N but has a number of N lower than the reference threshold value, and is to be encoded according to the second encoding process, then each nucleotide or base of the read is individually encoded on 2 bits.

If a read comprises at least one N but with a number of N greater than the reference threshold value, then said read is in any case encoded according to the second encoding process, and each nucleotide or base of the read is individually encoded on 4 bits. In this case, the encoding step 12 does not comprise encoding and storing a list of positions of the N in the reference sequence. Indeed, each N mismatch is then directly encoded according to the second encoding process, in the very same way as the other nucleotides or bases of the read.

The first and third encoding processes comprise distinct sets of descriptors. Each set of descriptors univocally represents the reads associated to the corresponding encoding process, each of the first and third encoding processes being a reduced information entropy encoding process. More precisely, the third encoding process comprises a first encoding subprocess and a second encoding subprocess. The imperfectly mapped reads that are determined to be globally mapped during step 4 are encoded according to the first encoding subprocess. The imperfectly mapped reads that are determined to be locally mapped during step 4 are encoded according to the second encoding subprocess. The first and second encoding subprocesses comprise distinct sets of descriptors, each set of descriptors univocally representing the reads associated to the corresponding encoding subprocess.

The alignment information encoded for each read, and which enables the reconstruction of the whole read sequence during the decompression of the data, then depends on the corresponding encoding process or subprocess used for said read. For example, the descriptors used for the first encoding process may be:

the absolute starting position of the perfectly mapped read with respect to the reference sequence (encoded on 16 or 32 bits), and the length of the read (encoded with differential coding relative to the length of the previous read, with variable length code ranging from 2 bits to 34 bits).

The descriptors used for the first encoding subprocess may be:

the absolute starting position of the imperfectly mapped read with respect to the reference sequence (encoded on 16 or 32 bits), the length of the read (encoded with differential coding relative to the length of the previous read, with variable length code ranging from 2 bits to 34 bits), and a list of the mismatches of the read.

The descriptors used for the second encoding subprocess may be:

the absolute starting position of the imperfectly mapped portion of the read with respect to the reference sequence—also called local alignment starting position (encoded on 16 or 32 bits), the length of the read (encoded with differential coding relative to the length of the previous read, with variable length code ranging from 2 bits to 34 bits), a list of the mismatches of the read, and the length of the clipped portions of the read that are not part of the alignment (encoded on 8 bits for each clipped portion).

Preferably, the list of mismatches which is encoded in first and second subprocesses comprises a header (bit flag, encoded on 1 byte). The five first bits of the byte are used to encode the number of mismatches contained in the read (in the preferred embodiment wherein the threshold value is equal to 31, said number is within the range [0-31]). One bit is then used to encode whether the imperfectly mapped read is globally or locally mapped. Another bit is used to encode whether or not the 2-bit mode is activated for the second encoding process. The last bit is used to encode whether or not the 4-bit mode is activated for the second encoding process. Preferably, for each read encoded according to the second encoding subprocess during the encoding step 12, the clipped portions of said read (i.e. those portions that are not part of the local alignment) are concatenated, and each nucleotide or base of said clipped portions is individually encoded. In a preferred embodiment, each nucleotide or base of such clipped portions of the read is individually encoded on 2 bits.

In a preferred embodiment, each mismatch encoded in the list of mismatches of an imperfectly mapped read (i.e. encoded according to the first or second encoding subprocess) is encoded on 1 byte. More precisely, each mismatch of an imperfectly mapped read that is to be encoded according to the first or second encoding subprocess may be encoded as follows:

the two first bits of the byte are used to encode the alternate nucleotide or base present in the read instead of the corresponding reference nucleotide or base in the reference sequence, the six last bits are used to encode the position of the mismatch in the reference sequence, said position being computed as an offset from the previous mismatch of the read (relative position of the mismatch, except for the first mismatch of the read for which the absolute position is encoded). The range of this offset, which is encoded on 6 bits, is therefore [0-63].

Figures 2, 3, 4:
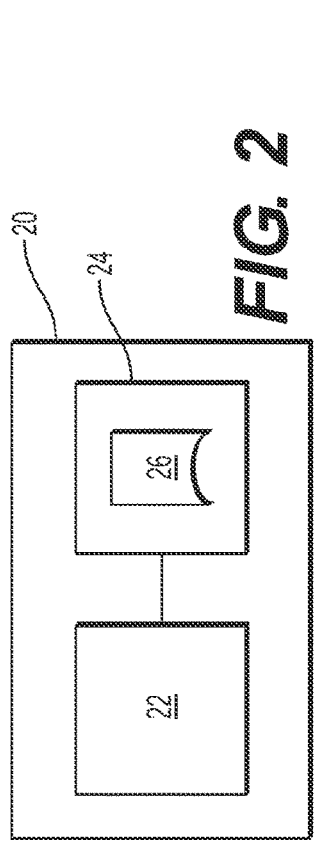
FIG. 2 is a diagram showing an apparatus for implementing the steps of the compression method according to the invention.
FIG. 3 shows a first example of a read that is globally mapped with a reference sequence.
FIG. 4 shows a second example of a read that is globally mapped with a reference sequence, in a case where a fake mismatch has to be inserted.

FIG. 3 provides an example of the encoding of the mismatches of a read according to the first encoding subprocess. The read is an imperfectly mapped read, which is globally mapped with the reference sequence. The read has two mismatches:

a first mismatch, located in the $12^{th}$ position in the read, which consists in a substitution of a A nucleotide in the reference sequence by a T nucleotide in the read, and a second mismatch, located in the $21^{th}$ position in the read, which consists in a substitution of a C nucleotide in the reference sequence by a G nucleotide in the read.

The list of the mismatches of the read is then encoded as:

<12, T>, the value "12" corresponding to the absolute position of the first mismatch in the read, and <9, G>, the value "9" corresponding to the relative position of the second mismatch in the read, i.e. the offset between the second mismatch and the first mismatch.

<12, T> may for example be converted into the value "51" (encoded on 1 byte), and <9, G> may be converted into the value "38" (encoded on 1 byte). Such a byte encoding is obtained with:

$$\text{offset position} \times 4 + \text{nucleotide value(with } A=0, C=1, G=2, T=3)$$

Preferably, for each imperfectly mapped read that is to be encoded according to the first or second encoding subprocess, if the offset computed between a given mismatch of the read and the previous mismatch is greater than a maximum encodable value, then at least one "fake" mismatch is inserted between said two mismatches until every offset between each of said mismatches and the at least one "fake" mismatch is lower than said maximum encodable value. A "fake" mismatch is defined as a mismatch for which the bits of the byte used to encode the mismatch encode a nucleotide or base that is equal to the corresponding reference nucleotide or base in the reference sequence. In a preferred embodiment, though not to be construed as limiting the scope of the present invention, the maximum encodable value is equal to 63, corresponding to the maximum value that is encodable on 6 bits.

FIG. 4 provides an example of the encoding of the mismatches of a read according to the first encoding subprocess, in a case where a "fake" mismatch has to be inserted. The read is an imperfectly mapped read, which is globally mapped with the reference sequence. The read has two mismatches:

a first mismatch, located in the $22^{th}$ position in the read, which consists in a substitution of a A nucleotide in the reference sequence by a T nucleotide in the read, and a second mismatch, located in the $134^{th}$ position in the read, which consists in a substitution of a C nucleotide in the reference sequence by a G nucleotide in the read.

The position offset between the second and the first mismatches is of 112, which is greater than the maximum encodable value of 63. A "fake" mismatch therefore has to be inserted between the two mismatches, so that every offset between each of the mismatches and the "fake" mismatch is lower than said maximum encodable value. A "fake" mismatch with a T nucleotide (corresponding to a "real" T nucleotide in the reference sequence) is for example inserted in the $85^{th}$ position in the read. The position offset computed between the "fake" mismatch and the first mismatch is 63, which is corresponds to the maximum encodable value. The position offset computed between the second mismatch and the "fake" mismatch is of 49, which is lower than 63.

The list of the mismatches of the read is then encoded as:

<22, T>, the value "22" corresponding to the absolute position of the first mismatch in the read, <63, T>, the value "63" corresponding to the relative position of the "fake" mismatch in the read, i.e. the offset between the "fake" mismatch and the first mismatch, and <49, G>, the value "49" corresponding to the relative position of the second mismatch in the read, i.e. the offset between the second mismatch and the "fake" mismatch.

<22, T> may for example be converted into the value "91" (encoded on 1 byte), <63, T> may be converted into the value "255" (encoded on 1 byte), and <49, G> may be converted into the value "198" (encoded on 1 byte). Such a byte encoding is obtained with:

$$\text{offset position} \times 4 + \text{nucleotide value (with } A=0, C=1, G=2, T=3)$$

The method comprises a final step 14 of providing a compressed file comprising a list of encoded reads. The encoded reads are stored in the compressed file in the same order as that of the reads stored in the initial uncompressed file. Each read can then be reconstructed from the alignment encoded information and the reference sequence, by a proper decompression software and/or method configured according to the present invention.

Although described with reference to an exemplary architecture of a computing device 20 (shown in FIG. 2 for illustrative purposes), the inventive techniques herewith disclosed may be implemented in hardware, software, firmware or any combination thereof. When implemented in software, the computer program code may be stored on a computer medium and executed by a hardware processing unit comprising one or more processors, as is the case with the device 20 of FIG. 2. It should be understood that the term "processor" as used herein is intended to include one or more processing devices, including a signal processor, a microprocessor, a microcontroller, an application-specific integrated circuit (ASIC), a field programmable gate array (FPGA) or other type of processing circuitry, as well as portions or combinations of such circuitry elements. Also, the term "memory" as used herein is intended to include electronic memory associated with a processor, such as random access memory (RAM), read-only memory (ROM) or other types of memory, in any combination.

Accordingly, software instructions or code for performing the methodologies and protocols described herein may be stored in one or more of the associated memory devices, e.g., ROM, fixed or removable memory, and, when ready to be utilized, loaded into RAM and executed by the processor.

The techniques of this disclosure may be implemented in a wide variety of devices or apparatuses, including for example mobile phones, computers, servers, tablets and similar devices.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

Statistical and Numerical Examples of the Compression Method According to the Invention The following comparative example has been performed on an uncompressed data file that contained 48 million reads or sequences of nucleotides:

size of the uncompressed data file: 35,770 MB (Mega-Byte)

size of the file that has been compressed with the gzip software: 6,649 MB size of the file that has been compressed with the non reference-based SPRING software: 1,402 MB size of the file that has been compressed with the reference-based compression method according to the present invention: 1,179 MB compression time with the non reference-based SPRING software: 1,722 s compression time with the reference based-compression method according to the present invention: 181 s average size in Bit/Nucleotide of the uncompressed data file (ASCII encoding): 8 bit/nucleotide average size in Bit/Nucleotide of the file that has been compressed with a coding adapted to 4 possible characters A, T, C, G: 2 bit/nucleotide average size in Bit/Nucleotide of the file that has been compressed with the reference-based compression method according to the present invention: 0.33 bit/nucleotide The numerical examples indicated above illustrate that the present invention allows for fast compression and decompression, while providing a high compression ratio.

What is claimed is:

1. A method for compressing genomic sequence data, the method comprising:

obtaining, by one or more computers, a read record;

determining, by the one or more computers, that the read record corresponds to a read that is imperfectly mapped to the reference sequence;

determining, by the one or more computers, that a number of mismatches of the imperfectly mapped read does not exceed a predetermined threshold number of mismatches;

obtaining, by the one or more computers, an offset from a previous mismatch that is lower than a maximum encodable offset value, wherein the maximum encodable offset value corresponds to a size of a portion of a field of a compressed read record that is to be allocated for storing the obtained offset; and encoding, by the one or more computers, each mismatch of the imperfectly mapped read and the offset from the previous mismatch of the read into a compressed read record having a size of 1 byte.

2. The method of claim 1, wherein the method further comprises:

obtaining, by the one or more computers, an additional read record;

determining, by the one or more computers, that the additional read record corresponds to an additional read that is imperfectly mapped to the reference sequence;

determining, by the one or more computers, that a number of mismatches of the imperfectly mapped additional read exceeds the predetermined threshold number of mismatches; and encoding, by the one or more computers, each base of the imperfectly mapped additional read individually in a compressed read record for the additional read.

3. The method of claim 1, wherein each read record comprises:

data indicating an absolute starting position of an aligned read with respect to the reference sequence;

data indicating a length of the read;

data indicating whether the read is perfectly mapped or imperfectly mapped;

data indicating a number of mismatches identified in the read; and data indicating a relative position of each of said mismatches in the read.

4. The method of claim 1, wherein encoding each mismatch of the imperfectly mapped read into a compressed read record having a size of 1 byte comprises, for each particular mismatch:

encoding, by the one or more computers, a first two bits of the byte to include data representing an alternate nucleotide or base present in the read instead of a corresponding reference nucleotide or base in the reference sequence; and encoding, by one or more computers, six remaining bits of the byte to include data representing the offset.

5. The method of claim 4, the method further comprising:

determining, by one or more computers, that the offset is greater than a maximum encodable value; and inserting, by one or more computers, at least one fake mismatch between the particular mismatch and the previous mismatch.

6. The method of claim 1, the method further comprising:

obtaining, by the one or more computers, an additional read record;

determining, by the one or more computers, that the additional read record corresponds to an additional read that is perfectly mapped to the reference sequence;

encoding, by one or more computers, at least a portion of the additional read record into a compressed read record for the additional read using reduced information entropy encoding.

7. A hardware processor that includes hardware processing circuitry that is configured to perform one or more operations, the one or more operations comprising:

obtaining, by the hardware processing circuitry, a read record;

determining, by the hardware processing circuitry, whether the read record corresponds to a read that is perfectly mapped to a reference sequence or imperfectly mapped to the reference sequence;

based on determining, by the hardware processing circuitry, that the read record corresponds to a read that is imperfectly mapped to the reference sequence, determining, by the one or more computers, whether a number of mismatches of the imperfectly mapped read does not exceed a predetermined threshold number of mismatches; and based on determining that the number of mismatches does not exceed the predetermined threshold number of mismatches, (i) obtaining, by the hardware processing circuitry, an offset from a previous mismatch that is lower than a maximum encodable offset value, wherein the maximum encodable offset value corresponds to a size of a portion of a field of a compressed read record that is to be allocated for storing the obtained offset and (ii) encoding, by the hardware processing circuitry, each mismatch of the imperfectly mapped read and the offset from the previous mismatch of the read into a compressed read record having a size of 1 byte.

8. The hardware processor of claim 7, wherein each read record comprises:

data indicating an absolute starting position of the aligned read with respect to the reference sequence;

data indicating a length of the read;

data indicating whether the read is perfectly mapped or imperfectly mapped;

data indicating a number of mismatches identified in the read; and data indicating a relative position of said mismatches in the read.

9. The hardware processor of claim 7, wherein encoding each mismatch of the imperfectly mapped read into a compressed read record having a size of 1 byte comprises for each particular mismatch:

encoding, by the hardware processing circuitry, a first two bits of the byte to include data representing an alternate nucleotide or base present in the read instead of a corresponding reference nucleotide or base in the reference sequence; and encoding, by the hardware processing circuitry, a six remaining bits of the byte to include data representing the offset.

10. The hardware processor of claim 9, wherein the hardware processor circuitry is further configured to perform operations comprising:

determining, by the hardware processing circuitry, whether the offset is greater than a maximum encodable value;

based on determining that the offset is greater than the maximum encodable value, inserting, by the hardware processing circuitry, at least one fake mismatch between the particular mismatch and the previous mismatch.

11. The hardware processor of claim 7, wherein the hardware processor circuitry is further configured to perform operations comprising:

based on determining that the read record corresponds to a read that is perfectly mapped to the reference sequence, encoding, by the hardware processing circuitry, at least a portion of the read record using reduced information entropy encoding.

12. The hardware processor of claim 7 wherein the hardware processing circuitry comprises one or more field programmable gate arrays (FPGAs).

13. The hardware processor of claim 7, wherein the one or more operations further comprise:

determining, by the hardware processing circuitry, that the number of mismatches of the imperfectly mapped read exceeds the predetermined threshold number of mismatches; and based on determining that that the number of mismatches of the imperfectly mapped read exceeds the predetermined threshold number of mismatches, encoding each base of the imperfectly mapped read individually.

14. A system for compressing genomic sequence data, the system comprising:

one or more computers and one or more storage devices storing instructions that are operable, when executed by one or more computers, to cause the one or more computers to perform the operations comprising:

obtaining, by the one or more computers, a read record;

determining, by the one or more computers, whether the read record corresponds to a read that is perfectly mapped to a reference sequence or imperfectly mapped to the reference sequence;

based on determining, by the one or more computers, that the read record corresponds to a read that is imperfectly mapped to the reference sequence, determining, by the one or more computers, whether a number of mismatches of the imperfectly mapped read does not exceed a predetermined threshold number of mismatches; and based on determining that the number of mismatches does not exceed the predetermined threshold number of mismatches, (i) obtaining, by the one or more computers, an offset from a previous mismatch that is lower than a maximum encodable offset value and (ii) encoding, by the one or more computers, each mismatch of the imperfectly mapped read and the offset from the previous mismatch of the read into a record having a size of 1 byte.

15. The system of claim 14, wherein each read record comprises:

data indicating an absolute starting position of an aligned read with respect to the reference sequence;

data indicating a length of the read;

data indicating whether the read is perfectly mapped or imperfectly mapped;

data indicating a number of mismatches identified in the read; and data indicating a relative position of each of said mismatches in the read.

16. The system of claim 14, wherein encoding each mismatch of the imperfectly mapped read into a record having a size of 1 byte comprises, for each particular mismatch:

encoding, by one or more computers, a first two bits of the byte to include data representing an alternate nucleotide or base present in the read instead of a corresponding reference nucleotide or base in the reference sequence; and encoding, by one or more computers, six remaining bits of the byte to include data representing the offset.

17. The system of claim 16, the operations further comprising:

determining, by the one or more computers, whether the offset is greater than a maximum encodable value; and based on determining that the offset is greater than the maximum encodable value, inserting, by one or more computers, at least one fake mismatch between the particular mismatch and the previous mismatch.

18. The system of claim 14, the operations further comprising:

based on determining that the read record corresponds to a read that is perfectly mapped to the reference sequence, encoding, by one or more computers, at least a portion of the read record using reduced information entropy encoding.

19. The system of claim 14, wherein the one or more computers comprises one or more hardware processors.

20. The system of claim 19 wherein the one or more hardware processors comprises one or more field programmable gate arrays (FPGAs).

21. The system of claim 14, wherein the operations further comprise:

determining, by the hardware processing circuitry, that the number of mismatches of the imperfectly mapped read exceeds the predetermined threshold number of mismatches; and based on determining that that the number of mismatches of the imperfectly mapped read exceeds the predetermined threshold number of mismatches, encoding each base of the imperfectly mapped read individually in a compressed read record.

22. A non-transitory computer-readable storage device having stored thereon instructions, which, when executed by a data processing apparatus, cause the data processing apparatus to perform operations for compressing genomic sequence data, the operations comprising:

obtaining a read record;

determining whether the read record corresponds to a read that is perfectly mapped to a reference sequence or imperfectly mapped to the reference sequence;

based on determining that the read record corresponds to a read that is imperfectly mapped to the reference sequence, determining whether a number of mismatches of the imperfectly mapped read does not exceed a predetermined threshold number of mismatches; and based on determining that the number of mismatches does not exceed the predetermined threshold number of mismatches, (i) obtaining an offset from a previous mismatch that is lower than a maximum encodable offset value, wherein the maximum encodable offset value corresponds to a size of a portion of a field of a compressed read record that is to be allocated for storing the obtained offset and (ii) encoding each mismatch of the imperfectly mapped read and the offset from the previous mismatch of the read into a compressed read record having a size of 1 byte.

23. The non-transitory computer-readable storage device of claim 22, wherein each read record comprises:

data indicating an absolute starting position of an aligned read with respect to the reference sequence;

data indicating a length of the read;

data indicating whether the read is perfectly mapped or imperfectly mapped;

data indicating a number of mismatches identified in the read; and data indicating a relative position of each of said mismatches in the read.

24. The non-transitory computer-readable storage device of claim 22, wherein encoding each mismatch of the imperfectly mapped read into a compressed read record having a size of 1 byte comprises, for each particular mismatch:

encoding, by one or more computers, a first two bits of the byte to include data representing an alternate nucleotide or base present in the read instead of a corresponding reference nucleotide or base in the reference sequence; and encoding, by one or more computers, six remaining bits of the byte to include data representing the offset.

25. The non-transitory computer-readable storage device of claim 24, the operations further comprising:

determining, by the one or more computers, whether the offset is greater than a maximum encodable value; and based on determining that the offset is greater than the maximum encodable value, inserting, by one or more computers, at least one fake mismatch between the particular mismatch and the previous mismatch.

26. The non-transitory computer-readable storage device of claim 22, the operations further comprising:

based on determining that the number of mismatches does not satisfy the predetermined threshold number of mismatches, encoding a list of positions of the reference sequence corresponding to a position of each of the mismatches to the reference sequence using a reduced information entropy encoding process.

27. The non-transitory computer-readable storage device of claim 22, the operations further comprising:

based on determining that the read record corresponds to a read that is perfectly mapped to the reference sequence, encoding at least a portion of the read record into a compressed read record using reduced information entropy encoding.

28. The non-transitory computer-readable storage device of claim 22, wherein the operations further comprise:

determining, by the hardware processing circuitry, that the number of mismatches of the imperfectly mapped read exceeds the predetermined threshold number of mismatches; and based on determining that that the number of mismatches of the imperfectly mapped read exceeds the predetermined threshold number of mismatches, encoding each base of the imperfectly mapped read individually in a compressed read record.

* * * * *